United States Patent
Yoo et al.

(10) Patent No.: US 9,747,686 B2
(45) Date of Patent: Aug. 29, 2017

(54) METHOD AND APPARATUS FOR CHANGING AT LEAST ONE OF DIRECTION AND POSITION OF PLANE SELECTION LINE BASED ON PATTERN

(71) Applicant: SAMSUNG MEDISON CO., LTD., Gangwon-Do (KR)

(72) Inventors: Jun-sang Yoo, Gangwon-Do (KR); Sung-yoon Kim, Gangwon-Do (KR)

(73) Assignee: SAMSUNG MEDISON CO., LTD., Hongcheon-gun, Gangwon-do (KR)

( * ) Notice: Subject to any disclaimer, the term of this patent is extended or adjusted under 35 U.S.C. 154(b) by 0 days.

(21) Appl. No.: 14/591,799

(22) Filed: Jan. 7, 2015

(65) Prior Publication Data

US 2015/0262353 A1 Sep. 17, 2015

(30) Foreign Application Priority Data

Mar. 17, 2014 (KR) .................. 10-2014-0031159

(51) Int. Cl.
*G06K 9/00* (2006.01)
*A61B 8/00* (2006.01)
(Continued)

(52) U.S. Cl.
CPC .............. *G06T 7/0012* (2013.01); *A61B 8/14* (2013.01); *A61B 8/466* (2013.01); *A61B 8/469* (2013.01);
(Continued)

(58) Field of Classification Search
USPC ........ 382/100, 103, 106–107, 128–134, 154, 382/162, 168, 173, 181, 190–199, 209,
(Continued)

(56) References Cited

U.S. PATENT DOCUMENTS

| 7,883,467 B2 | 2/2011 | Akaki et al. |
| 2005/0049494 A1 | 3/2005 | Gritzky et al. |

(Continued)

FOREIGN PATENT DOCUMENTS

| EP | 2700364 A2 | 2/2014 |
| JP | 2884218 B2 | 4/1999 |

(Continued)

OTHER PUBLICATIONS

Extended European Search Report dated Aug. 19, 2015 issued in European Patent Application No. 14197361.0.
(Continued)

*Primary Examiner* — Seyed Azarian
(74) *Attorney, Agent, or Firm* — McDermott Will & Emery LLP

(57) ABSTRACT

Disclosed is a method of changing at least one of a direction and position of a plane selection line for acquiring an image of a plane of interest of an object. The method includes acquiring a medical image of an object, displaying a first plane image acquired along a first plane selection line of the medical image, setting a pattern which is used to change at least one of the direction and position of the plane selection line, changing at least one of the direction and position of the plane selection line, based on the set pattern, and displaying a second plane image acquired along the changed plane selection line.

35 Claims, 14 Drawing Sheets

(51) Int. Cl.
*G06T 7/00* (2017.01)
*G06K 9/46* (2006.01)
*G06K 9/52* (2006.01)
*G06T 3/00* (2006.01)
*A61B 8/14* (2006.01)
*A61B 8/08* (2006.01)
*G01S 7/52* (2006.01)

(52) U.S. Cl.
CPC .............. *A61B 8/483* (2013.01); *A61B 8/523* (2013.01); *G06K 9/46* (2013.01); *G06K 9/52* (2013.01); *G06T 3/00* (2013.01); *G01S 7/5206* (2013.01); *G01S 7/52073* (2013.01); *G01S 7/52074* (2013.01); *G06K 2009/4666* (2013.01)

(58) Field of Classification Search
USPC ....... 382/232, 254, 274, 276, 285–296, 305, 382/312; 345/419; 600/443
See application file for complete search history.

(56) References Cited

U.S. PATENT DOCUMENTS

2011/0144499 A1* 6/2011 Yoo .......................... A61B 8/14
600/443
2011/0172531 A1* 7/2011 Kanayama ............. A61B 8/461
600/443
2011/0282207 A1* 11/2011 Hashimoto .......... A61B 8/0883
600/443
2012/0176365 A1* 7/2012 Hansegard ............. A61B 8/085
345/419
2014/0050381 A1* 2/2014 Lee ....................... A61B 8/5223
382/131

FOREIGN PATENT DOCUMENTS

| JP | 2006-141997 A | 6/2006 |
| JP | 2009-000361 A | 1/2009 |
| KR | 10-0978479 B1 | 8/2010 |
| KR | 2011-0068846 A | 6/2011 |

OTHER PUBLICATIONS

"Sonographic Examination of the Fetal Central Nervous System: Guidelines for Performing the 'Basic Examination' and the 'Fetal Neurosonogram'." The International Society of Ultrasound in Obstetrics & Gynecology; Ultrasound Obstet Gynecol, 2007; 29: 109-116; (published online at www.interscience.wiley.com and www.isuog.org).

* cited by examiner

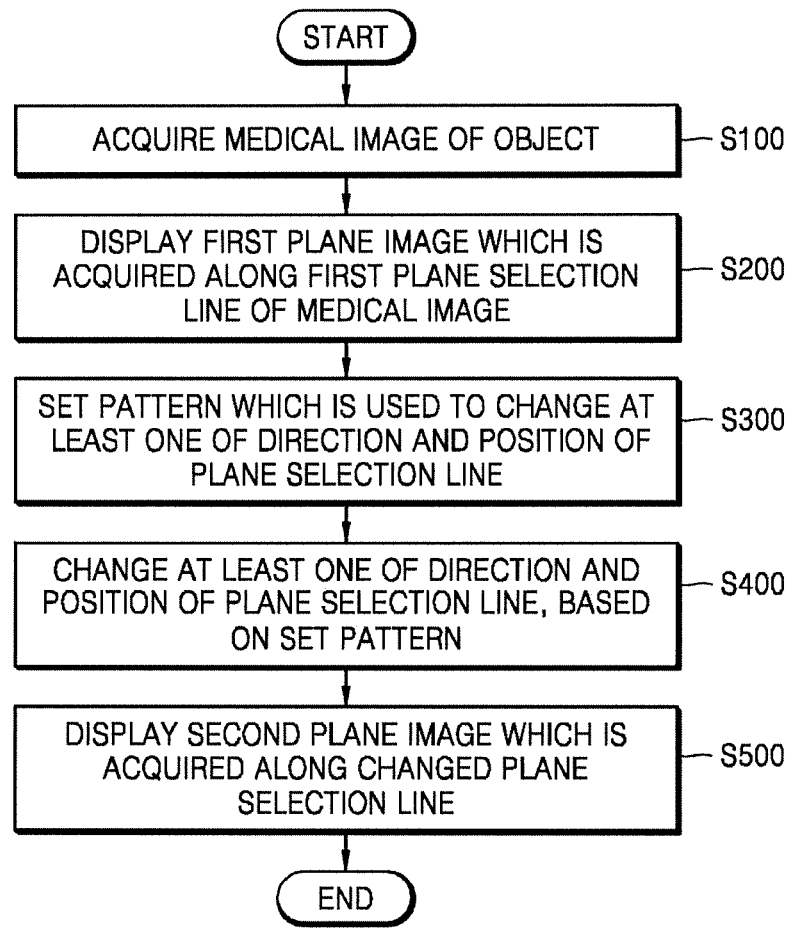

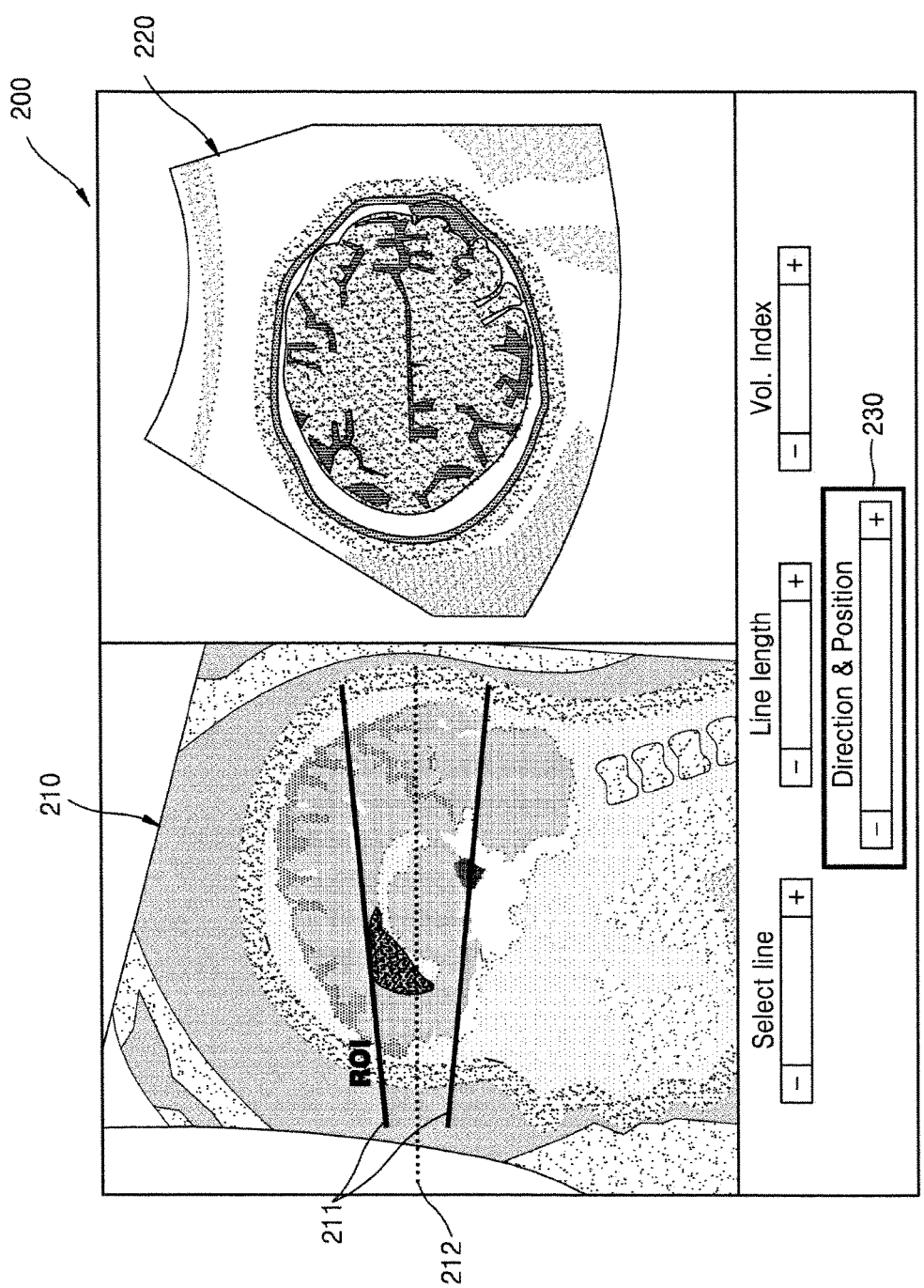

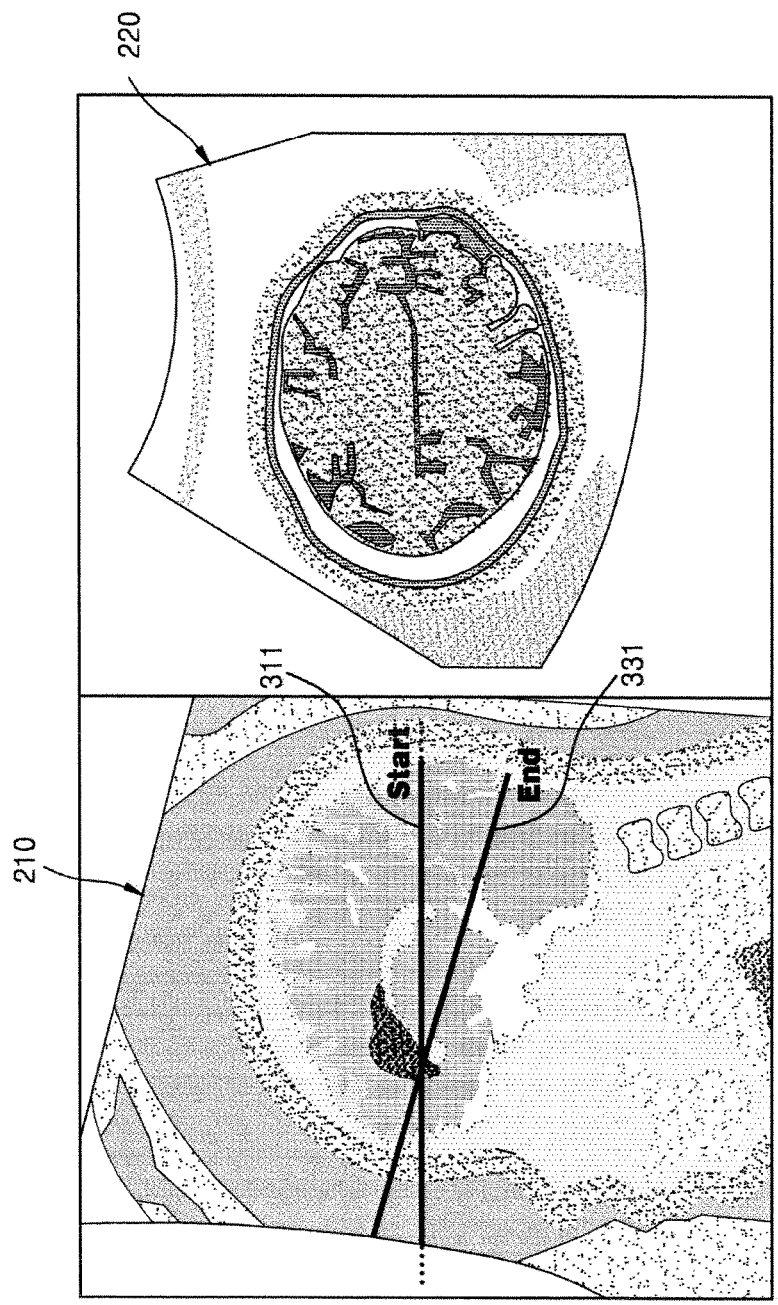

FIG. 5A
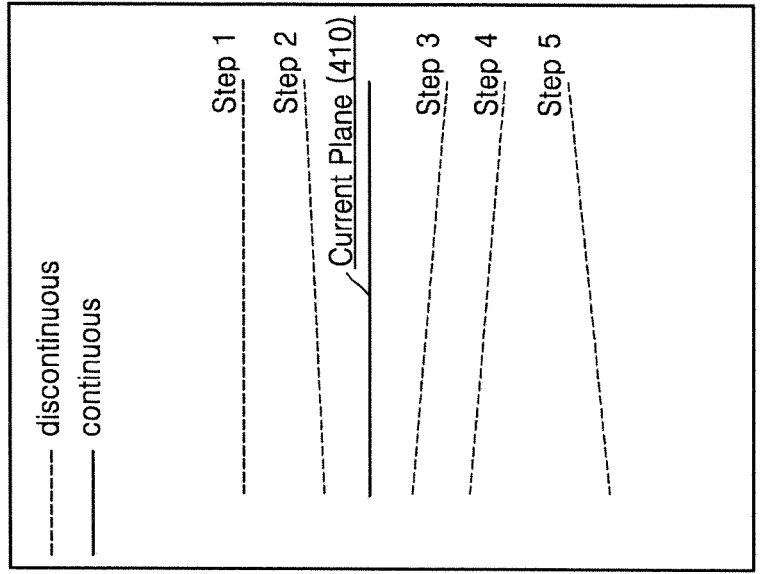
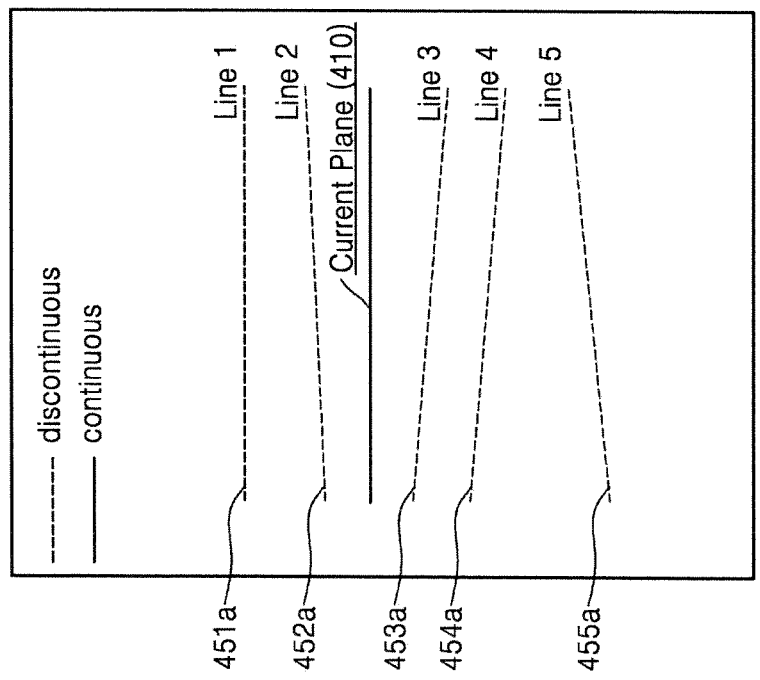

METHOD AND APPARATUS FOR CHANGING AT LEAST ONE OF DIRECTION AND POSITION OF PLANE SELECTION LINE BASED ON PATTERN

RELATED APPLICATION

This application claims the benefit of Korean Patent Application No. 10-2014-0031159, filed on Mar. 17, 2014, in the Korean Intellectual Property Office, the disclosure of which is incorporated herein in its entirety by reference.

BACKGROUND

1. Field

One or more embodiments of the present invention relate to a method and apparatus for changing at least one of a direction and position of a plane selection line, based on a pattern.

2. Description of the Related Art

Ultrasound diagnostic apparatuses transfer an ultrasound signal from a surface of an object to a certain part of a human body, and obtain a tomography image of a soft tissue or an image of blood flow by using information of an ultrasound signal reflected from an internal tissue of the human body.

In other words, ultrasound diagnostic apparatuses transmits an ultrasound signal, which is generated by a transducer of a probe, to an object, and receives information of an echo signal reflected from the object to obtain an image of an internal part of the object. The ultrasound diagnostic apparatuses display information about an object in real time. Also, ultrasound diagnostic apparatuses have high stability because an object is not exposed to X-rays or the like, and thus are being widely used along with other image diagnostic apparatuses such as X-ray diagnostic apparatuses, computerized tomography (CT) scanners, magnetic resonance imaging (MRI) apparatuses, and nuclear medicine diagnostic apparatuses.

SUMMARY

One or more embodiments of the present invention include a method of changing at least one of a direction and position of a plane selection line based on a pattern for acquiring an image of a plane of interest (POI) of an object.

Additional aspects will be set forth in part in the description which follows and, in part, will be apparent from the description, or may be learned by practice of the presented embodiments.

According to one or more embodiments of the present invention, a method of changing at least one of a direction and position of a plane selection line for acquiring an image of a plane of interest (POI) of an object includes: acquiring a medical image of an object; displaying a first plane image acquired along a first plane selection line of the medical image; setting a pattern which is used to change at least one of the direction and position of the plane selection line; changing at least one of the direction and position of the plane selection line, based on the set pattern; and displaying a second plane image acquired along the changed plane selection line, wherein the plane selection line is automatically or manually selected based on an anatomical position of a part of interest, a measurement target item, and an anatomical view in the object.

The medical image may include a two-dimensional (2D) image, a three-dimensional (3D) volume image, or a dynamic image.

The displaying of the first plane image may include displaying the medical image and first plane image of the object.

The setting of the pattern may include: determining a region of interest (ROI) including a first-direction plane selection line in the acquired medical image; generating at least one plane selection lines which have different directions or positions and are included in the determined ROI; extracting the generated at least one plane selection lines; and generating the pattern in order where the at least one plane selection lines are extracted.

The setting of the pattern may include: re-determining an ROI; regenerating at least one plane selection lines which have different directions or positions and are included in the re-determined ROI; re-extracting the regenerated at least one plane selection lines; and regenerating the pattern in order where the at least one plane selection lines are re-extracted, wherein an interval between the at least one plane selection lines when a plane selection line is regenerated may be denser than an interval of when the plane selection line is generated.

The setting of the pattern may include: extracting the first plane selection line, for a first standard image to be acquired as the first plane image; extracting a reference region from the acquired medical image; rotating the extracted first plane selection line by a certain angle based on the reference region to change the extracted first plane selection line to a second plane selection line; and generating, as the pattern, a rotation movement from the first plane selection line to the second plane selection line.

The setting of the pattern may include: generating at least one plane selection lines adjacent to the first plane selection line; extracting the generated at least one plane selection lines; and generating the pattern in order where the at least one plane selection lines are extracted.

The setting of the pattern may include: extracting the first plane selection line, for a first standard image to be acquired as the first plane image; generating at least one plane selection lines which are moved and disposed in a certain direction from the extracted first plane selection line; extracting the generated at least one plane selection lines; and generating the pattern in order where the at least one plane selection lines are extracted, wherein the certain direction may include at least one of an up direction, a down direction, a left direction, a right direction, and a diagonal direction.

The setting of the pattern may include: extracting a reference region from the acquired medical image; generating at least one plane selection lines which pass through the reference region and are within a certain angle range; extracting the generated at least one plane selection lines; and generating the pattern in order where the at least one plane selection lines are rotated with respect to the reference region and extracted.

The setting of the pattern may include: generating at least one plane selection lines in order where an external input signal is applied; extracting the at least one plane selection lines in order where the at least one plane selection lines are generated; and generating the pattern in order where the at least one plane selection lines are extracted.

The setting of the pattern may include: generating a second plane selection line adjacent to the first plane selection line, based on an external input signal; generating at least one plane selection lines which are provided between the first and second plane selection lines; sequentially extracting at least one plane selection lines, which are provided between the first and second selection lines, while moving lines in a certain direction from the first plane selection line to the second plane selection line; and generating a pattern for changing a line in order where the at least one plane selection lines are extracted, wherein the certain direction may include at least one of an up direction, a down direction, a left direction, a right direction, and a diagonal direction.

The setting of the pattern may include loading a pattern which is predetermined and is previously stored in a storage device, and setting a pattern for changing at least one of the direction and position of the plane selection line, based on the loaded pattern.

The changing of at least one of the direction and position of the plane selection line may include changing at least one of the direction and position of the plane selection line based on the set pattern automatically or according to an external input.

The changing of at least one of the direction and position of the plane selection line may include: tracing at least one of the direction and position of the plane selection line which is changed based on the set pattern; and displaying the trace result as a time-series image.

The method may further include: selecting a first point from the acquired medical image according to a first external input and selecting a second point according to a second external input; generating a first plane selection line including the selected first and second points; and displaying information about a pattern which is set for changing at least one of the direction and position of the plane selection line, wherein, the first plane selection line may be moved according to a third external input in the acquired medical image, based on the displayed information, and a plane image may be acquired along the moved first plane selection line.

According to one or more embodiments of the present invention, an apparatus for changing at least one of a direction and position of a plane selection line for acquiring an image of a plane of interest (POI) of an object includes: a medical image acquiring unit that acquires a medical image of an object; a display that displays a first plane image acquired along a first plane selection line of the medical image; a pattern setting device that sets a pattern which is used to change at least one of the direction and position of the plane selection line; and a line changing device that changes at least one of the direction and position of the plane selection line, based on the set pattern, wherein, the display displays a second plane image acquired along the changed plane selection line, and the plane selection line is automatically or manually selected based on an anatomical position of a part of interest, a measurement target item, and an anatomical view in the object.

The medical image may include a two-dimensional (2D) image, a three-dimensional (3D) volume image, or a dynamic image.

The display may display the medical image and first plane image of the object.

The pattern setting device may determine an ROI including a first-direction plane selection line in the acquired medical image, generate at least one plane selection lines which have different directions or positions and are included in the determined ROI, extract the generated at least one plane selection lines, and generate the pattern in order where the at least one plane selection lines are extracted.

The pattern setting device may re-determine an ROI, regenerates at least one plane selection lines which have different directions or positions and are included in the re-determined ROI, re-extract the regenerated at least one plane selection lines, and regenerate the pattern in order where the at least one plane selection lines are re-extracted, and an interval between the at least one plane selection lines when a plane selection line is regenerated may be denser than an interval of when the plane selection line is generated.

The pattern setting device may extract the first plane selection line, for a first standard image to be acquired as the first plane image, extract a reference region from the acquired medical image, rotate the extracted first plane selection line by a certain angle based on the reference region to change the extracted first plane selection line to a second plane selection line, and generate, as the pattern, a rotation movement from the first plane selection line to the second plane selection line.

The pattern setting device may generate at least one plane selection lines adjacent to the first plane selection line, extract the generated at least one plane selection lines, and generate the pattern in order where the at least one plane selection lines are extracted.

The pattern setting device may extract the first plane selection line, for a first standard image to be acquired as the first plane image, generate at least one plane selection lines which are moved and disposed in a certain direction from the extracted first plane selection line, extract the generated at least one plane selection lines, and generate the pattern in order where the at least one plane selection lines are extracted, and the certain direction may include at least one of an up direction, a down direction, a left direction, a right direction, and a diagonal direction.

The pattern setting device may extract a reference region from the acquired medical image, generate at least one plane selection lines which pass through the reference region and are within a certain angle range, extract the generated at least one plane selection lines, and generate the pattern in order where the at least one plane selection lines are rotated with respect to the reference region and extracted.

The apparatus may further include an external input receiving unit, wherein the pattern setting device may generate at least one plane selection lines in order where an external input signal is applied, extract the at least one plane selection lines in order where the at least one plane selection lines are generated, and generate the pattern in order where the at least one plane selection lines are extracted.

The pattern setting device may generate a second plane selection line adjacent to the first plane selection line, based on an external input signal, generate at least one plane selection lines which are provided between the first and second plane selection lines, sequentially extract at least one plane selection lines, which are provided between the first and second selection lines, while moving lines in a certain direction from the first plane selection line to the second plane selection line, and generate a pattern for changing a line in order where the at least one plane selection lines are extracted, and the certain direction may include at least one of an up direction, a down direction, a left direction, a right direction, and a diagonal direction.

The pattern setting device may load a pattern which is predetermined and is previously stored in a storage device, and set a pattern for changing at least one of the direction and position of the plane selection line, based on the loaded pattern.

The apparatus may further include an external input receiving unit, wherein the line changing device may change at least one of the direction and position of the plane selection line based on the set pattern automatically or according to an external input.

The line changing device may trace at least one of the direction and position of the plane selection line which is changed based on the set pattern, and the display may display the trace result as a time-series image.

The pattern setting device may select a first point from the acquired medical image according to a first external input, selects a second point according to a second external input, and generates a first plane selection line including the selected first and second points, the display may display information about a pattern which is set for changing at least one of the direction and position of the plane selection line, the first plane selection line may be moved according to a third external input in the acquired medical image, based on the displayed information, and a plane image may be acquired along the moved first plane selection line.

According to one or more embodiments of the present invention, provided is a non-transitory computer-readable storage medium storing a program for executing the method.

BRIEF DESCRIPTION OF THE DRAWINGS

These and/or other aspects will become apparent and more readily appreciated from the following description of the embodiments, taken in conjunction with the accompanying drawings in which:

FIG. 1 is a flowchart illustrating a method of changing at least one of a direction and position of a plane selection line, according to an embodiment of the present invention;

FIGS. 2A and 2B illustrate an example of a method of determining a region of interest (ROI) and changing at least one of a direction and position of a plane selection line based on a pattern which is generated based on the determined ROI, according to an embodiment of the present invention;

FIGS. 3A and 3B illustrate an example of a method of changing at least one of a direction and position of a plane selection line based on a generated pattern, according to another embodiment of the present invention;

FIGS. 5A to 5D illustrate an example of a generated pattern according to another embodiment of the present invention;

DETAILED DESCRIPTION

Figure 2B:
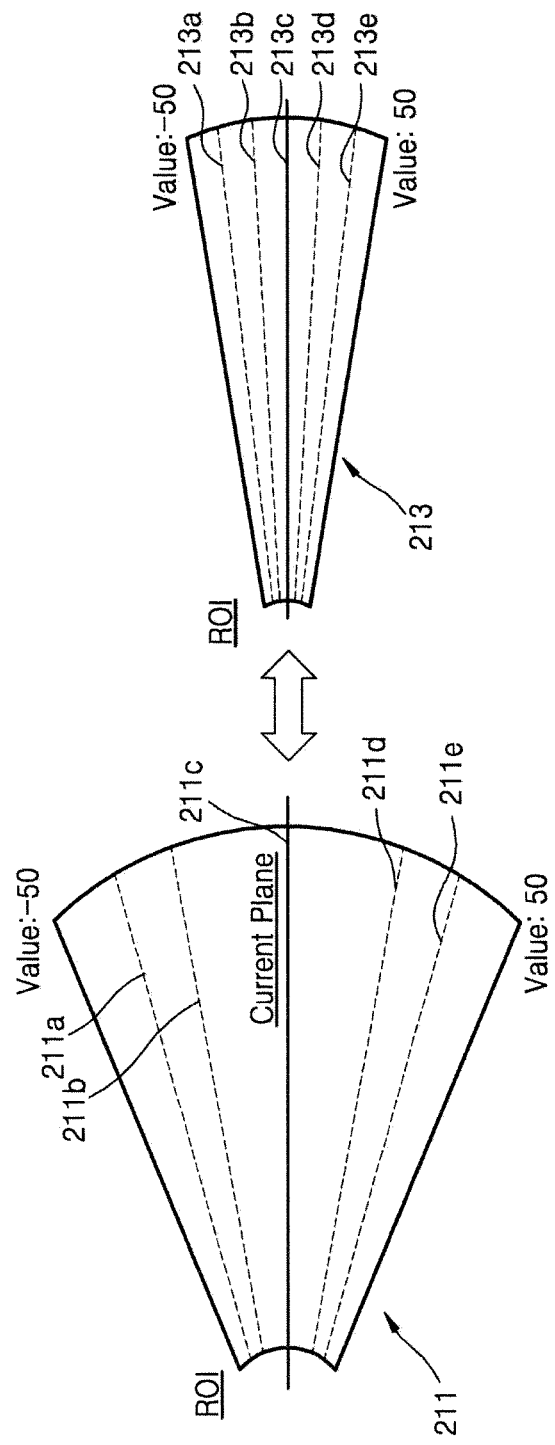

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Hereinafter, the terms used in the specification will be briefly described, and then the present invention will be described in detail.

The terms used in this specification are those general terms currently widely used in the art in consideration of functions in regard to the present invention, but the terms may vary according to the intention of those of ordinary skill in the art, precedents, or new technology in the art. Also, specified terms may be selected by the applicant, and in this case, the detailed meaning thereof will be described in the detailed description of the invention. Thus, the terms used in the specification should be understood not as simple names but based on the meaning of the terms and the overall description of the invention.

Throughout the specification, it will also be understood that when a component "includes" an element, unless there is another opposite description thereto, it should be understood that the component does not exclude another element but may further include another element. In addition, terms such as " . . . unit", " . . . module", or the like refer to units that perform at least one function or operation, and the units may be implemented as hardware or software or as a combination of hardware and software.

Throughout the specification, the term "medical image" may denote an ultrasonic image, an X-ray image, a magnetic resonance (MR) image, or a computerized tomography (CT) image. An "ultrasonic image" refers to an image of an object obtained using an ultrasonic wave.

In the present specification, "object" may include a person or an animal, or a part of a person or an animal. For example, the object may include the liver, the heart, the womb, the brain, a breast, the abdomen, or a blood vessel. Furthermore, the "object" may include a phantom. The phantom means a material having a volume that is approximately the intensity and effective atomic number of a living thing, and may include a spherical phantom having a property similar to a human body.

Moreover, the term "user" used herein is a medical expert, and may be a doctor, a nurse, a medical technologist, a medical image expert, or the like, or may be an engineer repairing a medical apparatus. However, the user is not limited thereto.

Reference will now be made in detail to embodiments, examples of which are illustrated in the accompanying drawings. In this regard, the present embodiments may have different forms and should not be construed as being limited to the descriptions set forth herein. In the following description, well-known functions or constructions are not described in detail since they would obscure the embodiments with unnecessary detail. Like reference numerals refer to like elements throughout.

A user of a medical apparatus may perform various measurements depending on the kind of examination and an examination item, for examining an object. For example, the user may measure various examination items (for example, bi-parietal diameter (BPD), occipito frontal diameter (OFD), femur length (FL), head circumference (HC), posterior ventricle diameter (Vp), cerebellum diameter (CBLL), and cisterna magna (CM)) for determining a growth state and malformation of a fetus. Also, a user may acquire a measurement value converted into a percentile, based on a data table including an internationally predefined recommendation value, and check a state of a fetus by using the percentile. In addition, the user may predict an age of the fetus by using a value of a measured examination item (for example, crown to rump length (CRL) or head circumference (HC)).

Therefore, it is important for a user to accurately find a region of interest (ROI) (for example, a plane of interest (POI)), for accurately measuring an examination item of an object.

According to an embodiment of the present invention, a pattern for changing at least one of a direction and position of a plane selection line may be set, and when selecting a plane, a user may quickly and accurately detect an ROI (for example, a POI) by using the pattern.

FIG. 1 is a flowchart illustrating a method of changing at least one of a direction and position of a plane selection line, according to an embodiment of the present invention.

A method of changing at least one of a direction and position of a plane selection line for acquiring an image of a POI of an object, according to an embodiment of the present invention, may include operation S100 of acquiring a medical image of an object, operation S200 of displaying a first plane image acquired along a first plane selection line of the medical image, operation S300 of setting a pattern which is used to change at least one of the direction and position of the plane selection line, operation S400 of changing at least one of the direction and position of the plane selection line, based on the set pattern, and operation S500 of displaying a second plane image acquired along the changed plane selection line.

The plane selection line according to an embodiment of the present invention may be automatically or manually selected based on an anatomical position of a part of interest, a measurement target item, and an anatomical view in the object. The direction or position of the plane selection line according to an embodiment of the present invention may be referred to as a geometry of the plane selection line.

In operation S100, the method may receive an echo signal based on an ultrasound wave, which is transmitted from a probe of an ultrasound diagnostic apparatus to the object, to acquire an ultrasound image of the object. The ultrasound image according to an embodiment of the present invention may be at least one of a brightness (B) mode image, a color (C) mode image, a Doppler (D) mode image, but is not limited thereto. Also, according to an embodiment of the present invention, the medical image may include a two-dimensional (2D) image, a three-dimensional (3D) volume image, or a dynamic image. For example, a plane image may be acquired from a rendered image (for example, a 3D volume image) which is obtained by using ultrasound 3D data, based on the plane selection line. Also, the plane selection line may be expressed as a plane selection surface in a VCT mode of 3D data.

Operation S200 of displaying the first plane image acquired along the first plane selection line of the medical image, according to an embodiment of the present invention, may include an operation of displaying the medical image and first plane image of the object. In other words, the medical image and first plane image of the object may be displayed in parallel. The displaying of the medical image and first plane image of the object in parallel denotes that the images may be arranged in a certain direction and displayed in parallel with each other. The certain direction may include at least one of an up direction, a down direction, a left direction, a right direction, and a diagonal direction.

The pattern for changing at least one of the direction and position of the plane selection line may be previously set and stored in a storage device (not shown), or may be set (S300) based on an external input from a user.

According to an embodiment of the present invention, at least one of the direction and position of the plane selection line may be changed based on the set pattern in operation S400, and the second plane image acquired along the changed plane selection line may be displayed by a display in operation S500.

The first and second plane images according to an embodiment of the present invention may be images that are acquired along the plane selection line, in a direction vertical to a medical image 210.

At least one of the direction and position of the plane selection line may be changed by using the following Equation (1):

$$x' = ax + ey + iz + m$$

$$y' = bx + fy + jz + n$$

$$z' = cx + gy + kz + o \qquad (1)$$

Equation (1) may be expressed as a matrix in the following Equation (2):

$$\begin{bmatrix} x' \\ y' \\ z' \end{bmatrix} = \begin{bmatrix} a & e & i & m \\ b & f & j & n \\ c & g & k & o \end{bmatrix} \times \begin{bmatrix} x \\ y \\ z \\ 1 \end{bmatrix} \qquad (2)$$

where x, y, and z may be coordinate values in a space where a 3D image is expressed and which is composed of an x axis, a y axis, and a z axis. The pattern for changing at least one of the direction and position of the plane selection line, according to an embodiment of the present invention, may be expressed as a 3×4 matrix as in Equation (2).

A parallel movement of a line according to an embodiment of the present invention may be achieved by a parallel movement conversion of a point included in the line. For example, a position of the line may be changed by changing the coordinate values (for example, x, y, and z) in the space composed of the x axis, the y axis, and the z axis with respect to the object as expressed in the following Equation (3):

$$\begin{bmatrix} 1 & 0 & 0 & tx \\ 0 & 1 & 0 & ty \\ 0 & 0 & 1 & tz \\ 0 & 0 & 0 & 1 \end{bmatrix} \qquad (3)$$

Moreover, a rotation movement of the line according to an embodiment of the present invention may be achieved by a rotation movement conversion of the point included in the line. For example, For example, a direction of the line may be changed by changing the coordinate values (for example, x, y, and z) in the space composed of the x axis, the y axis, and the z axis with respect to the object as expressed in the following Equation (4):

$$\begin{bmatrix} \cos\Theta & 0 & \sin\Theta & 0 \\ 0 & 1 & 0 & 0 \\ -\sin\Theta & 0 & \cos\Theta & 0 \\ 0 & 0 & 0 & 1 \end{bmatrix} \qquad (4)$$

Moreover, a pattern for changing the line according to an embodiment of the present invention may be generated by a combination of a matrix of Equation (3) and a matrix of Equation (4).

The above-described method according to an embodiment of the present invention will be described below with reference to FIGS. 2A and 2B.

FIGS. 2A and 2B illustrate an example of a method of determining an ROI and changing at least one of a direction and position of a plane selection line based on a pattern which is generated based on the determined ROI, according to an embodiment of the present invention.

The medical image 210 of an object may be acquired in operation S100. For example, when the object is a fetus, the medical image of a head of the fetus may be acquired, and displayed on a screen 200.

As illustrated in FIG. 2A, a first plane image 220 acquired along a first plane selection line 212 in the medical image 210 may be displayed in operation S200. As described above, a user may perform various measurements depending on the kind of examination and an examination item for an object, for accurately performing a clinical determination of the object. It is important for the user to accurately find an ROI (for example, a POI), for accurately measuring an examination item (for example, bi-parietal diameter (BPD)) of the object. Therefore, the user may variously change at least one of a direction and position of a plane selection line to detect the POI. In this case, a pattern for detecting the POI is previously set, and the user may detect the POI by using the set pattern, thereby shortening a time taken in detecting the POI. Accordingly, an efficiency of a diagnosis by the user increases in comparison to that of the related art.

Operation S300 of setting the pattern for changing at least one of the direction and position of the plane selection line, according to an embodiment of the present invention, may include an operation of determining an ROI 211 including a first-direction plane selection line 212 in the acquired medical image 210, an operation of generating at least one plane selection lines which have different directions or positions and are included in the determined ROI 211, an operation of extracting the generated at least one plane selection lines, and an operation of generating a pattern in order where the at least one plane selection lines are extracted.

The ROI 211 according to an embodiment of the present invention, as illustrated in FIG. 2A, may have a fan shape in a width-direction. For example, the ROI 211 may be determined as a region which is unfolded at a certain angle within a certain range with respect to the first-direction plane selection line 212. The certain angle and the certain range may be previously determined based on at least one of the kind of examination and an examination item for the object. Also, the certain angle and the certain range may be set and adjusted according to an external input from the user.

Referring to FIG. 2B, at least one plane selection lines 211a to 211e which have different directions or positions and are included in the ROI 211 may be generated. Also, according to an embodiment of the present invention, the generated at least one plane selection lines 211a to 211e may be extracted one by one. A pattern for changing at least one of a direction and position of a plane selection line may be generated in order where the at least one plane selection lines 211a to 211e are extracted. For example, a plane may be extracted in the order of the plane selection line 211c, plane selection line 211b, plane selection line 211d, plane selection line 211a, and plane selection line 211e. The first-direction plane selection line 212 may be the plane selection line 211c, and hereinafter, may be referred to as a line indicating a currently displayed surface or plane 220. Since the plane may be extracted in the order of the plane selection line 211c, plane selection line 211b, plane selection line 211d, plane selection line 211a, and plane selection line 211e, a plane selection line may be changed in the order of the plane selection line 211c, plane selection line 211b, plane selection line 211d, plane selection line 211a, and plane selection line 211e. In the plane selection lines 211a to 211e, at least one of directions and positions may differ.

Moreover, at least one generated plane selection line according to an embodiment of the present invention may be removed based on an external input signal. For example, the plane selection line 211a or the plane selection line 211e may be removed from the ROI 211 according to a line removal signal which is input from the outside by the user. When the plane selection line 211a or the plane selection line 211e is removed, a plane selection line may be changed in the order of the plane selection line 211c, plane selection line 211b, and plane selection line 211d.

Operation S300 of setting the pattern for changing at least one of the direction and position of the plane selection line, according to an embodiment of the present invention, may further include an operation of re-determining an ROI, an operation of regenerating at least one plane selection lines which have different directions or positions and are included in the re-determined ROI, an operation of re-extracting the regenerated at least one plane selection lines, and an operation of regenerating the pattern in order where the at least one plane selection lines are re-extracted. An interval between the at least one plane selection lines when a plane selection line is regenerated may be denser than an interval of when the plane selection line is generated.

Referring to FIG. 2B, the ROI 211 may be re-determined as a new ROI 213. Regarding an ROI (for example, 213) having a narrow range, a pattern for changing at least one of a direction and position of a plane selection line may be more minutely generated than a pattern which is generated based on an ROI (for example, 211). When at least one plane selection lines 213a to 213e to be regenerated are regenerated to be included in the ROI 213, an interval between the regenerated at least one plane selection lines 213a to 213e may be denser than the interval between the plane selection lines 211a to 211e which are generated to be included in the ROI 211. Therefore, the user may re-determine the new ROI 213 by narrowing the ROI 211 which was previously determined, thereby allowing a more precise selection of a plane of the object and allowing a pattern, which is used to change at least one of a direction and position of a plane selection line, to be more minutely generated.

According to an embodiment of the present invention, at least one of the direction and position of the plane selection line may be changed based on the set pattern in operation S400, and the second plane image acquired along the changed plane selection line may be displayed by a display in operation S500.

Figure 3A:
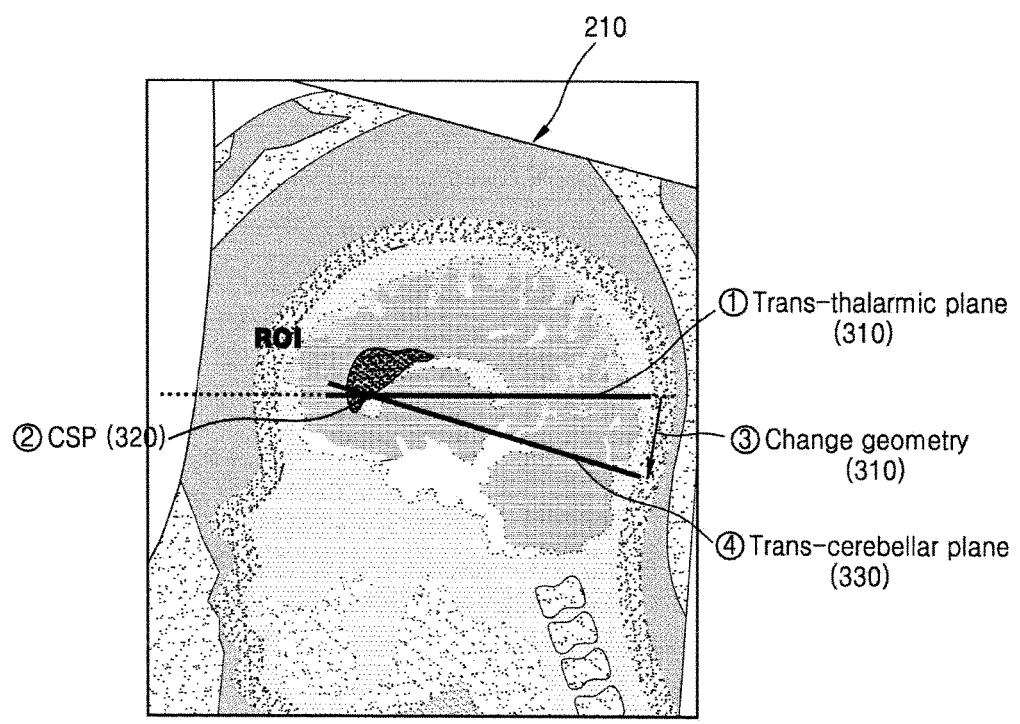

FIGS. 3A and 3B illustrate an example of a method of changing at least one of a direction and position of a plane selection line based on a generated pattern, according to another embodiment of the present invention.

Operation S300 of setting the pattern for changing at least one of the direction and position of the plane selection line, according to an embodiment of the present invention, may include an operation of extracting the first plane selection line, for a first standard image to be acquired as the first plane image, an operation of extracting a reference region from the acquired medical image, an operation of rotating the extracted first plane selection line by a certain angle based on the reference region to change the extracted first plane selection line to a second plane selection line, and an operation of generating, as a pattern, a rotation movement from the first plane selection line to the second plane selection line.

According to an embodiment of the present invention, a change pattern may be generated by using anatomical information of an object. For example, a first plane selection line 310 may be extracted from a medical image 210 in order for the first standard image to be acquired as the first plane image. The first standard image may be referred to as a first standard view. When the object is a brain, the first standard image may be an image indicating mid-sagittal plane, trans-ventricle plane, transthalamic plane, and transcerebellar plane. When the object is a heart, the first standard image may include four chamber views, five chamber views, three vessel views, RVOT, LVOT, a bicaval view, aortic arch, ductral arch, a high short axis view, and a low short axis view. When the object is a fetus, the first standard image may be an image may include a plane (or a view) for abdominal circumference (AC) measurement, a plane (or a view) for head circumference (HC) measurement, and a plane (or a view) for crown-rump length (CRL) measurement.

Moreover, a reference region 320 may be extracted from the acquired medical image 210. The reference region 320 is a position or a region which includes a unique tissue in the object, and may be referred to as a landmark. The reference region 320, for example, may include a cavum septum pellucidum (CSP). Moreover, according to an embodiment of the present invention, by changing the extracted first plane selection line 310 by a certain angle based on the reference region 320, the first plane selection line 310 may be changed to a second plane selection line 330. The second plane selection line 330 may be a line from which a trans-cerebellar plane is acquired. Also, according to an embodiment of the present invention, a rotation movement from the first plane selection line 310 to the second plane selection line 330 may be generated as a pattern. In other words, a first plane selection line (for example, a line from which a trans-thalamic plane is acquired) may be extracted, a reference region (for example, CSP) may be extracted, and the extracted first plane selection line may be rotated and moved with respect to the reference region, thereby generating a pattern in which the first plane selection line is changed to a second plane selection line (for example, a line from which a trans-cerebellar plane is acquired).

As described above, according to an embodiment of the present invention, a pattern may be generated based on a relationship (for example, a rotation movement of a certain angle) between a reference region, referred to as a landmark, and various views (for example, a first plane based on a first plane selection line and a second plane based on a second plane selection line). As illustrated in FIG. 3B, a plane selection line may be changed through a rotation movement from a start line 311 to an end line 331 according to a pattern in which the first plane selection line is set as a start line 311 and the second plane selection line is set as an end line 331 for changing a pattern, and thus, a plane 220 based on each line may be displayed.

FIGS. 4A to 4D illustrate an example of a generated pattern according to an embodiment of the present invention.

Figure 4A:
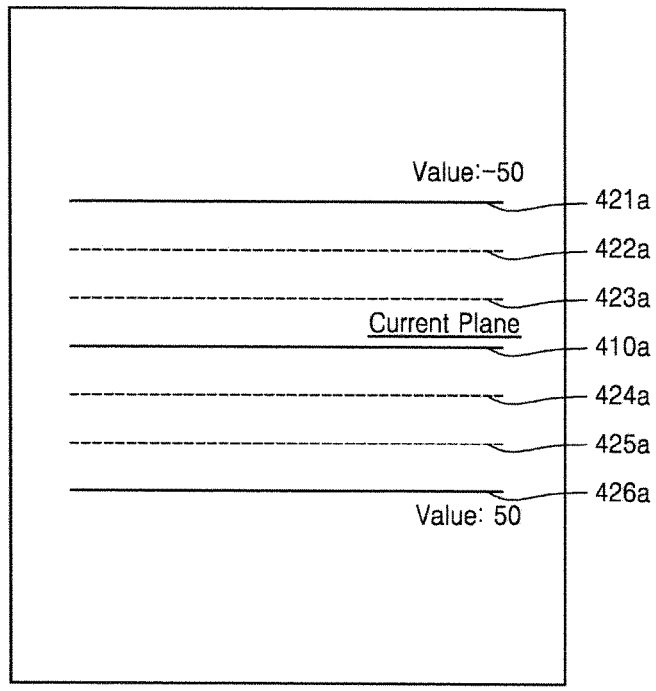
FIGS. 4A to 4D illustrate an example of a generated pattern according to an embodiment of the present invention.
Figure 4B:
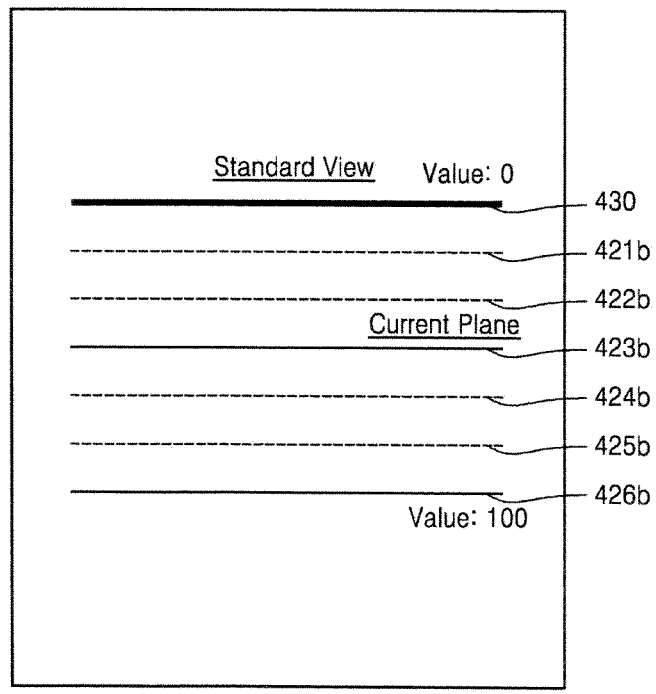

FIG. 4A illustrates an example of a generated basic change pattern according to an embodiment of the present invention.

Operation S300 of setting the pattern for changing at least one of the direction and position of the plane selection line, according to an embodiment of the present invention, may include an operation of generating at least one plane selection lines adjacent to the first plane selection line, an operation of extracting the generated at least one plane selection lines, and an operation of generating a pattern for changing a line in order where the at least one plane selection lines are extracted.

For example, as illustrated in FIG. 4A, at least one plane selection lines 421a to 426a may be generated adjacent to upper and lower positions with respect to a first plane selection line 410a that is a current line. The generated at least one plane selection lines 421a to 426a, for example, may be extracted sequentially or randomly from an upper end (or a lower end). For example, lines may be extracted in the order of the plane selection line 421a, plane selection line 422a, and plane selection line 423a. Also, lines may be randomly extracted, for example, in the order of the plane selection line 421a, plane selection line 425a, and plane selection line 423a. A pattern for changing a line may be generated in order where lines are extracted. In other words, a line may be moved or changed from a first plane selection line to at least one plane selection line disposed adjacent to the first plane selection line, and thus, a user may acquire a POI.

Operation S300 of setting the pattern for changing at least one of the direction and position of the plane selection line, according to an embodiment of the present invention, may include an operation of extracting the first plane selection line, for a first standard image to be acquired as the first plane image, an operation of generating at least one plane selection lines which are moved and disposed in a certain direction from the extracted first plane selection line, an operation of extracting the generated at least one plane selection lines, and an operation of generating a pattern for changing a line in order where the at least one plane selection lines are extracted. The certain direction may include at least one of an up direction, a down direction, a left direction, a right direction, and a diagonal direction.

A first plane selection line 430, from which the first standard image is acquired, may be referred to as a standard view line. The first standard image may include a mid-sagittal image or a trans-thalamic image. When the first plane selection line 430 for acquiring the first standard image is extracted, at least one plane selection lines 421b to 426b which are disposed to be spaced apart from the extracted first plane selection line 430 in a certain direction may be generated. For example, the at least one plane selection lines 421b to 426b which are disposed to be spaced apart from the first plane selection line 430 by a certain interval in a down direction may be generated. The certain interval may be an interval equal to a height of one pixel or two pixels.

Moreover, the at least one plane selection lines 421b to 426b which are generated in a certain direction (for example, a down direction) from the first plane selection line 430 may be extracted sequentially or randomly. For example, lines may be extracted in the order of the plane selection line 421b, plane selection line 422b, and plane selection line 423b. Also, lines may be randomly extracted, for example, in the order of the plane selection line 421b, plane selection line 425b, and plane selection line 423b. A pattern for changing a line may be generated in order where the at least one plane selection lines 421b to 426b are extracted.

Figure 4C:
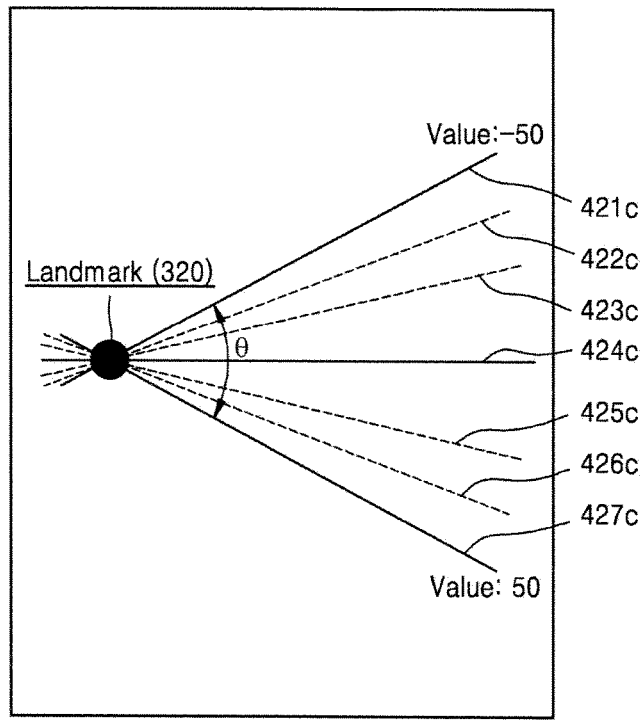

Operation S300 of setting the pattern for changing at least one of the direction and position of the plane selection line, according to an embodiment of the present invention, may include an operation of extracting a reference region from the acquired medical image, an operation of generating at least one plane selection lines which pass through the reference region and are within a certain angle range, an operation of extracting the generated at least one plane selection lines, and an operation of generating a pattern for changing a line in order where the at least one plane selection lines are rotated with respect to the reference region and extracted. As illustrated in FIG. 4C, a reference region 320 may be extracted from the medical image of the object. The reference region 320 is a position or a region which includes a unique tissue in the object, and may be referred to as a landmark. The reference region 320, for example, may include a CSP or a thalamus of a diencephalon. At least one plane selection lines 421c to 427c, which pass through the extracted reference region 320 and are within a certain angle range, may be generated. The generated at least one plane selection lines 421c to 427c may be rotated with respect to the reference region 320 and extracted sequentially or randomly. A pattern for changing a line may be generated in order where the at least one plane selection lines 421c to 427c are extracted.

Figure 4D:
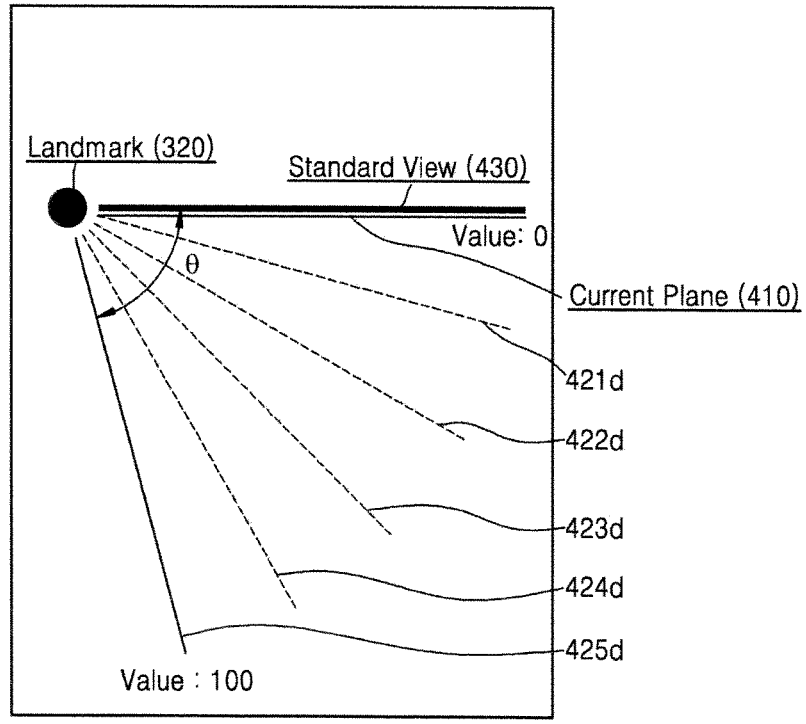

Moreover, according to an embodiment of the present invention, as illustrated in FIG. 4D, at least one plane selection lines 421d to 425d may be generated by rotating and moving a line 410 indicating a current plane (for example, 220 in FIG. 2A or 3B) by a certain angle based on a first plane selection line 430 (from which a first standard image is acquired) and a reference region 320 of an object. The generated at least one plane selection lines 421d to 425d may be extracted sequentially or randomly, and a pattern for changing a line may be generated in order where the plane selection lines 421d to 425d are extracted.

Moreover, according to an embodiment of the present invention, as illustrated in FIGS. 2A and 2B, a line change pattern may be set in order for a line to be changed depending on the at least one plane selection lines (for example, 211a to 211e or 213a to 213e) generated in the ROI 211 or 213. For example, the ROI 211 or 213 may be a region within a range having a high probability that includes a standard plane image acquirable in a position or a direction which is recommended by an international organization.

FIGS. 5A to 5D illustrate an example of a generated pattern according to another embodiment of the present invention.

Operation S300 of setting the pattern for changing at least one of the direction and position of the plane selection line, according to an embodiment of the present invention, may include an operation of generating at least one plane selection lines in order where an external input signal is applied, an operation of extracting the at least one plane selection lines in order where the at least one plane selection lines are generated, and an operation of generating a pattern for changing a line in order where the at least one plane selection lines are extracted.

As illustrated in FIG. 5A, at least one plane selection lines 451a to 455a may be generated based on an external input signal from a user. In other words, the at least one plane selection lines 451a to 455a may be generated in order where the external input signal is applied to the ultrasound diagnostic apparatus for generating a line. For example, a user may input the external input signal to the ultrasound diagnostic apparatus by using a cursor having an arrow shape or a linear-direction touch in a touch screen.

Moreover, a plane selection line may be extracted according to a generated order. For example, lines may be generated in the order of a line 451a, a line 452a, a line 453a, a line 454a, and a line 455a, and a plane selection line may be extracted according to the generated order. Also, a pattern (for example, step 1 to step 5 in FIG. 5A) for changing a line may be generated in order (for example, an order of from 451a to 455a) where at least one the plane selection lines are extracted. In other words, the pattern for changing the line may be generated as a pattern in which lines are discontinuously moved in the order of the line 451a, line 452a, line 453a, line 454a, and line 455a from a line 410 indicating a current plane image and thus are changed.

Operation S300 of setting the pattern for changing at least one of the direction and position of the plane selection line, according to an embodiment of the present invention, may include an operation of generating a second plane selection line adjacent to the first plane selection line, based on an external input signal, an operation of generating at least one plane selection lines which are provided between the first and second plane selection lines, an operation of sequentially extracting at least one plane selection lines, which are provided between the first and second selection lines, while moving lines in a certain direction from the first plane selection line to the second plane selection line, and an operation of generating a pattern for changing a line in order where the at least one plane selection lines are extracted. The certain direction may include at least one of an up direction, a down direction, a left direction, a right direction, and a diagonal direction.

Figure 5B:
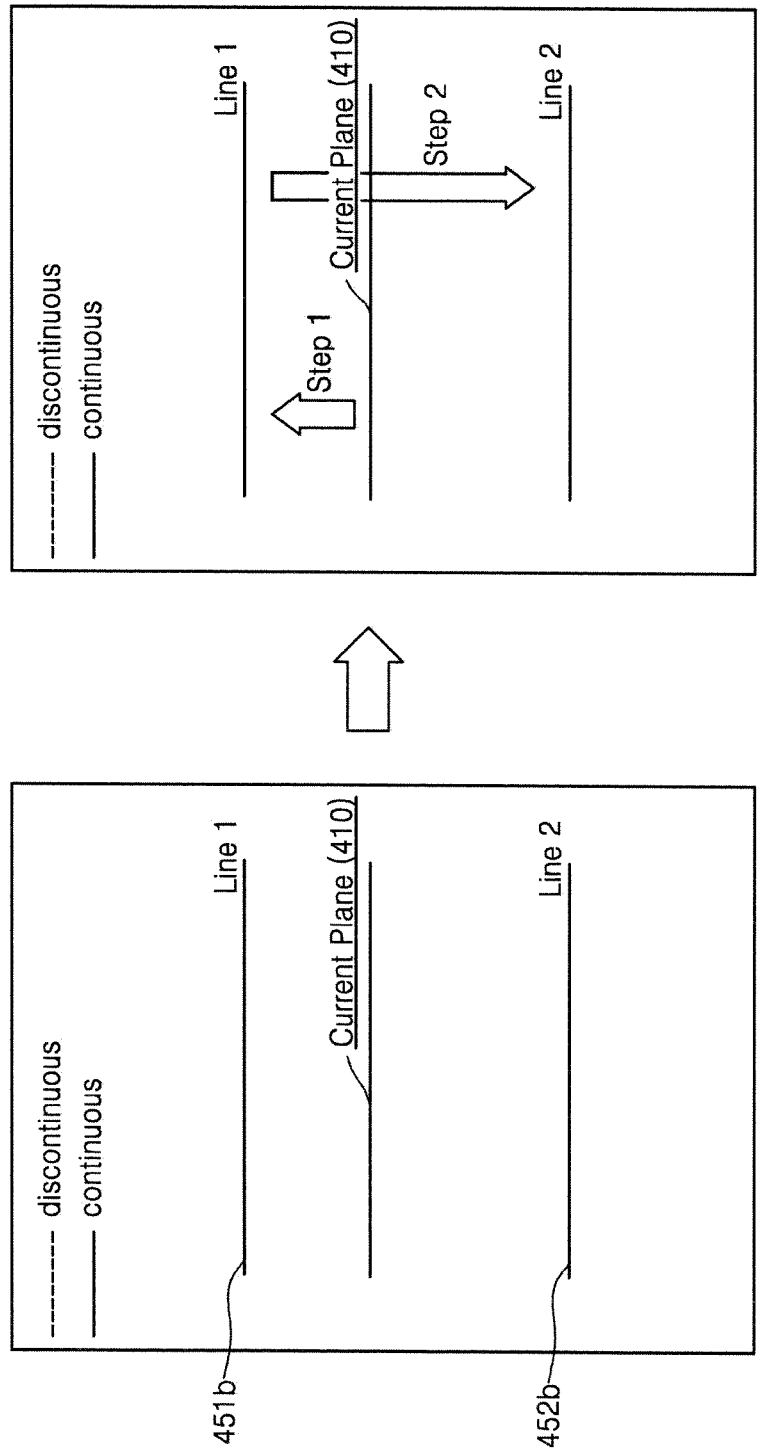

As illustrated in FIG. 5B, a second plane selection line adjacent to a first plane selection line may be generated based on an external input signal. The first plane selection line may be a line 410 from which a current plane image is acquired. Also, at least one plane selection lines (not shown) which are provided between a first plane selection line 410 and a second plane selection line 451b may be generated. Also, the at least one plane selection lines which are provided between the first plane selection line 410 and the second plane selection line 451b and moved in a certain direction from the first plane selection line 410 to the second plane selection line 451b may be sequentially extracted. A pattern for changing a line may be generated in order where the at least one plane selection lines are extracted.

For example, at least one plane selection lines (not shown) which have a certain thickness and are provided between the first plane selection line 410 and the second plane selection line 451b may be generated. The certain thickness may be the same as that of the first plane selection line 410 or second plane selection line 451b. The at least one plane selection lines which are provided between the first plane selection line 410 and the second plane selection line 451b and moved in an up direction from the first plane selection line 410 to the second plane selection line 451b may be sequentially extracted, and a pattern for changing a line may be generated in order where the at least one plane selection lines are extracted. Therefore, the pattern for changing the line may be set to be changed depending on all plane selection lines which are provided between the first plane selection line 410 and the second plane selection line 451b. In other words, as illustrated in FIG. 5B, the at least one plane selection lines which are provided between the first plane selection line 410 and the second plane selection line 451b and moved from the first plane selection line 410 (which is a line from which a current plane image is acquired) to the second plane selection line 451b may be continuously extracted, and a pattern for changing a line may be generated in order where the at least one plane selection lines are extracted. For example, a portion (for example, step 1 in FIG. 5B) of a pattern for changing a line may be generated in order where all lines (not shown), which are provided between the first plane selection line 410 and the second plane selection line 451b and moved in an up direction from the first plane selection line 410 to the second plane selection line 451*b*, are extracted. In this way, a portion (for example, step 2 in FIG. 5B) of the pattern for changing the line may be generated in order where all lines (not shown), which are provided between the second plane selection line 451*b* and a third plane selection line 452*b* and moved in a down direction from the second plane selection line 451*b* to the third plane selection line 452*b*, are extracted. A pattern (including the portion (for example, step 1 or step 2 in FIG. 5B) of the pattern described above with reference to FIG. 5B) for changing a line may be generated. In other words, the pattern for changing the line may be generated by combining step 1 and step 2 of FIG. 5B.

Figure 5C:
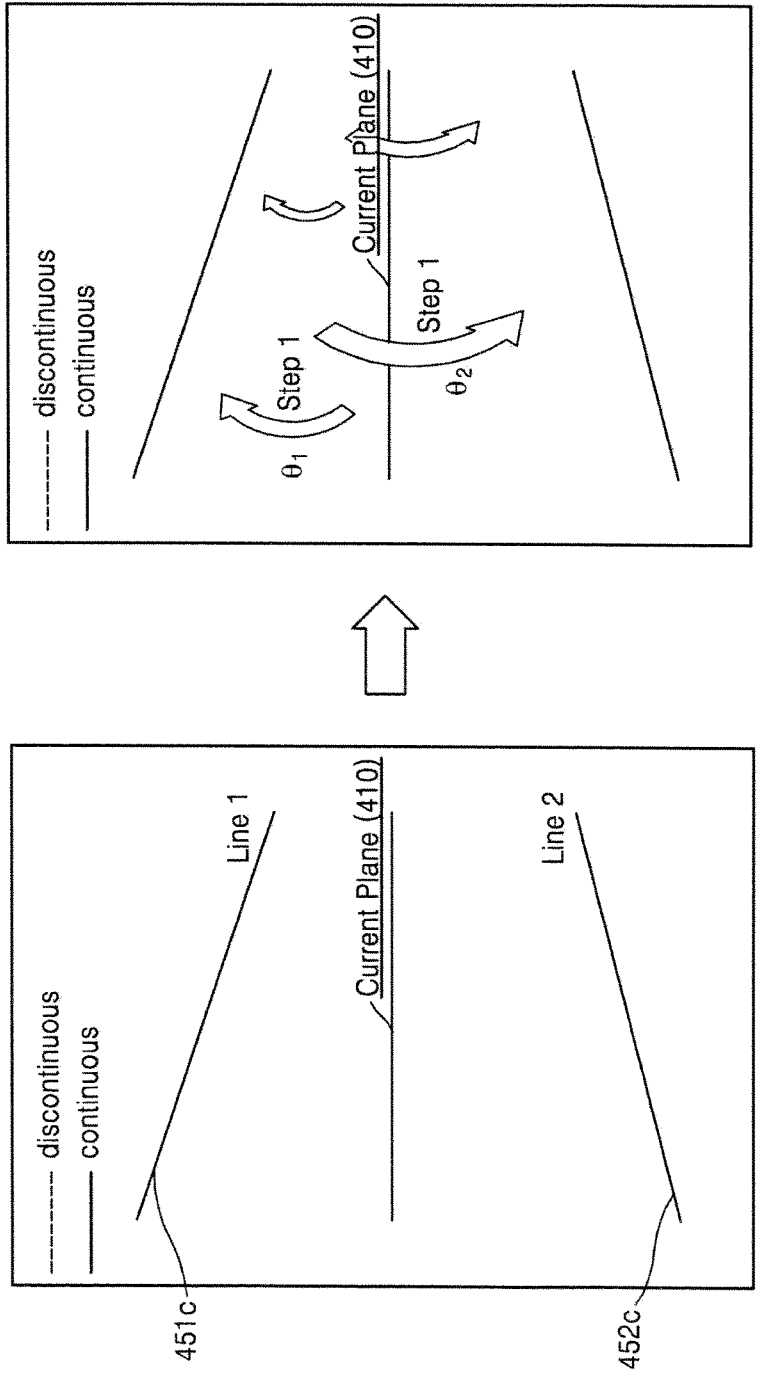
Figure 5D:
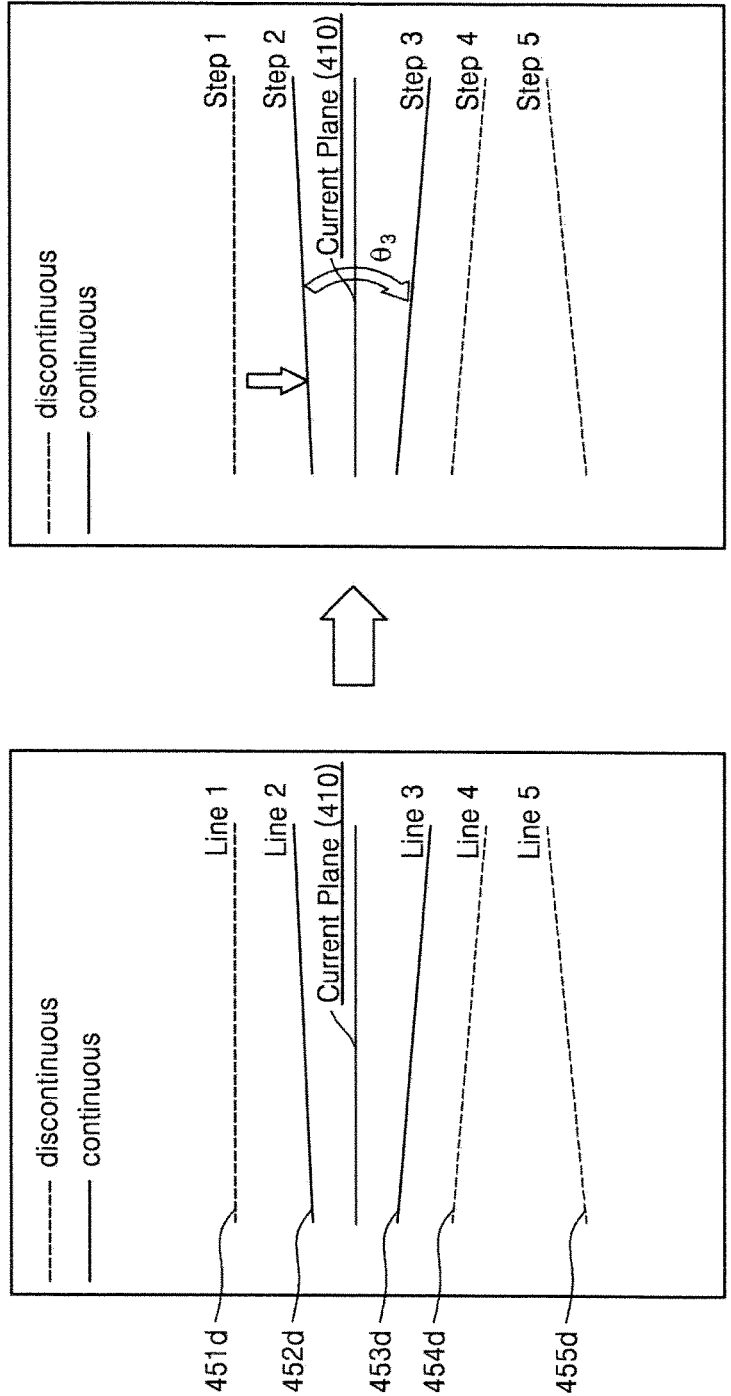

Moreover, according to another embodiment of the present invention, as illustrated in FIG. 5C, a second plane selection line which is disposed adjacent to a first plane selection line in a certain direction may be generated based on an external input signal. The first plane selection line may be a line 410 from which a current plane image is acquired. Also, at least one plane selection lines (not shown) provided between a first plane selection line 410 and a second plane selection line 451*c* may be generated. In addition, at least one plane selection lines which are provided between the first plane selection line 410 and the second plane selection line 451*c* and are rotated and moved by a certain angle to the second plane selection line 451*c* with respect to the first plane selection line 410 may be sequentially extracted, and a pattern for changing a line may be generated in order where the at least one plane selection lines are extracted.

A pattern for changing a line may be set to be changed along all plane selection lines which are provided between the first plane selection line 410 and the second plane selection line 451*c*. In other words, as illustrated in FIG. 5C, at least one plane selection lines which are provided between the first plane selection line 410 and the second plane selection line 451*c* and are rotated and moved by a certain angle "$\theta_1$" from the first plane selection line 410 to the second plane selection line 451*c* may be continuously extracted, and a portion (step 1) of a pattern for changing a line may be generated in order where the at least one plane selection lines are extracted. Also, at least one plane selection lines which are provided between the second plane selection line 451*c* and a third plane selection line 452*c* and are rotated and moved by a certain angle "$\theta_2$" from the second plane selection line 451*c* to the third plane selection line 452*c* may be continuously extracted, and a portion (step 2) of a pattern for changing a line may be generated in order where the at least one plane selection lines are extracted. A pattern (including the portion (for example, step 1 or step 2 in FIG. 5C) of the pattern described above with reference to FIG. 5C) for changing a line may be generated. In other words, the pattern for changing the line may be generated by combining step 1 and step 2 of FIG. 5C.

Moreover, according to an embodiment of the present invention, a pattern may be generated by combining the above-described methods of changing a line. For example, a pattern in which a line is discontinuously moved (for example, step 1) from the first plane selection line 410 (which is a line from which a current plane image is acquired) to a line 451*d*, a line is continuously moved (for example, step 2) from the line 451*d* to a line 452*d*, a line is rotated and moved by a certain angle "$\theta_3$" from the line 452*d* to a line 453*d*, and a line is discontinuously moved (step 4 and step 5) to a line 454*d* and a line 455*d* may be generated as a pattern for changing a line.

Operation S300 of setting the pattern for changing at least one of the direction and position of the plane selection line, according to an embodiment of the present invention, may include an operation of loading a pattern which is predetermined and is previously stored in a storage device (not shown), and setting a pattern, based on the loaded pattern. For example, a pattern which is predetermined and is previously stored in a storage device may be loaded, and the loaded pattern may be set as a pattern for changing at least one of a direction and position of a plane selection line. Also, the loaded pattern may be edited by the above-described method, and may be set as a pattern for changing at least one of a direction and position of a plane selection line.

Operation S400 of changing at least one of the direction and position of the plane selection line based on the set pattern, according to an embodiment of the present invention, may include an operation of changing at least one of the direction and position of the plane selection line based on the set pattern automatically or according to an external input.

For example, at least one from among the direction and position of the plane selection line may be automatically changed based on the set pattern. In other words, although an external input is separately applied, at least one from among the direction and position of the plane selection line may be automatically changed based on the set pattern in operation S400, and the second plane image acquired along the changed plane selection line may be displayed by a display in operation S500.

Moreover, an orientation adjusting unit (for example, 230 in FIG. 2A) may be adjusted according to an external input, and at least one from among a direction and position of a plane selection line may be easily changed based on a pattern. In the related art, an up, down, left, and right rotation movement of a 3D image of an object are performed on an x axis, a y axis, and a z axis a plurality of times, for acquiring a POI. However, according to an embodiment of the present invention, the orientation adjusting unit (for example, 230 in FIG. 2A) may be adjusted according to an external input applied by a user, and thus, at least one from among a direction and position of a plane selection line may be easily changed based on a pattern generated by the above-described method. The orientation adjusting unit may be, for example, a controller including a bar and a rotation button as in 230 of FIG. 2A.

Operation S400 of changing at least one from among the direction and position of the plane selection line based on the set pattern, according to an embodiment of the present invention, may further include an operation of tracing at least one from among the direction and position of the plane selection line which are changed based on the set pattern and an operation of displaying a result of the tracing as a time-series image. For example, a pattern (which is generated by the above-described method) for changing a line may be displayed as a time-series image. A user may analyze the pattern displayed as the time-series image, and correct the pattern by adding or deleting a line.

A trace result of a pattern for changing a line may be displayed as a time-series image, and thus, it is easy to analyze an anatomical structure of an object. For example, a plane image based on lines adjacent to a line from which a current plane is acquired may be displayed in time series, and thus, a longest region or largest region of an object may be detected. For example, when a line indicating a trans-ventricular plane is traced and displayed, a user may check whether Vp is clearly included in a currently displayed plane image (for example, 220) and whether Vp is the largest shown. Also, when a line indicating a trans-cerebellar plane is traced and displayed in time series, a user may check whether TCD is clearly included in a currently displayed plane image (for example, 220) and whether TCD is the largest shown.

Figure 6A:
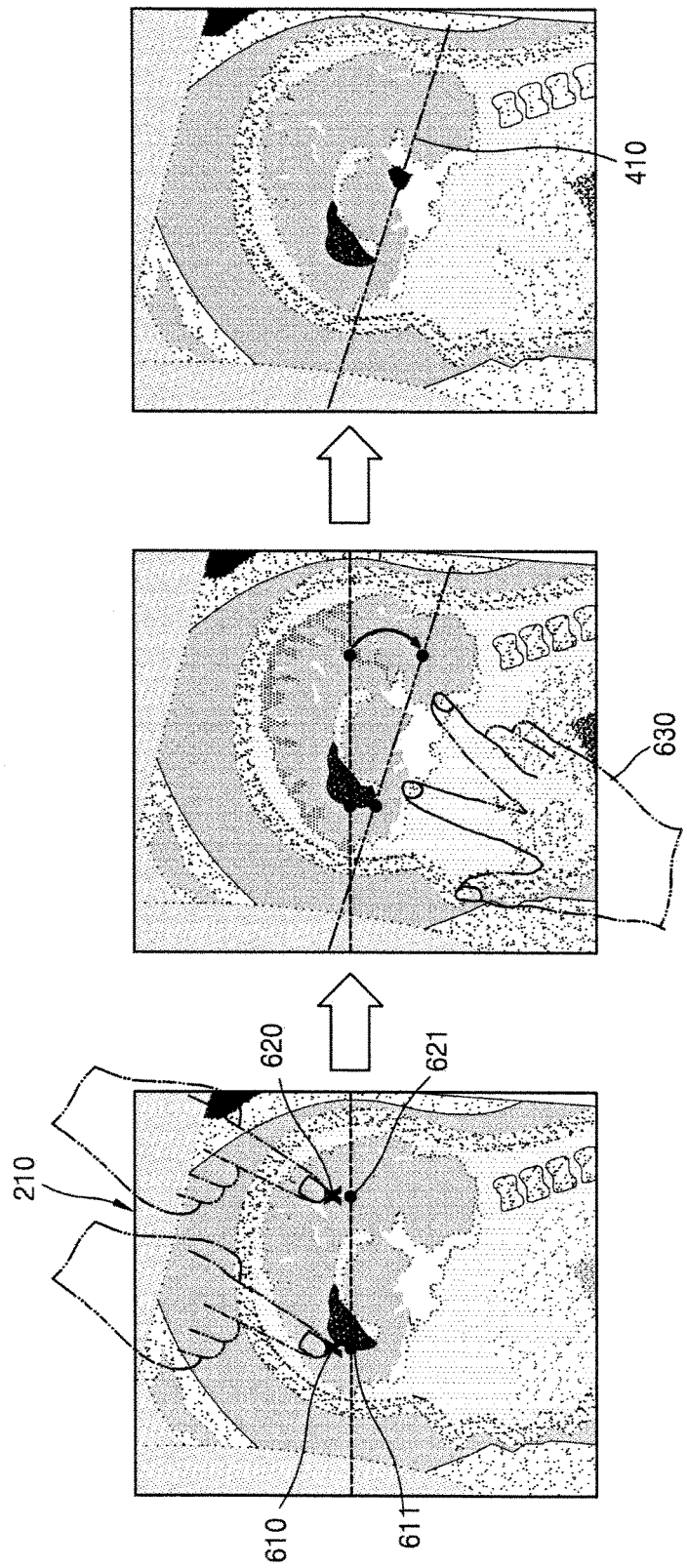
FIGS. 6A and 6B illustrate an example of a method of changing a plane selection line based on an external input, according to an embodiment of the present invention.
Figure 6B:
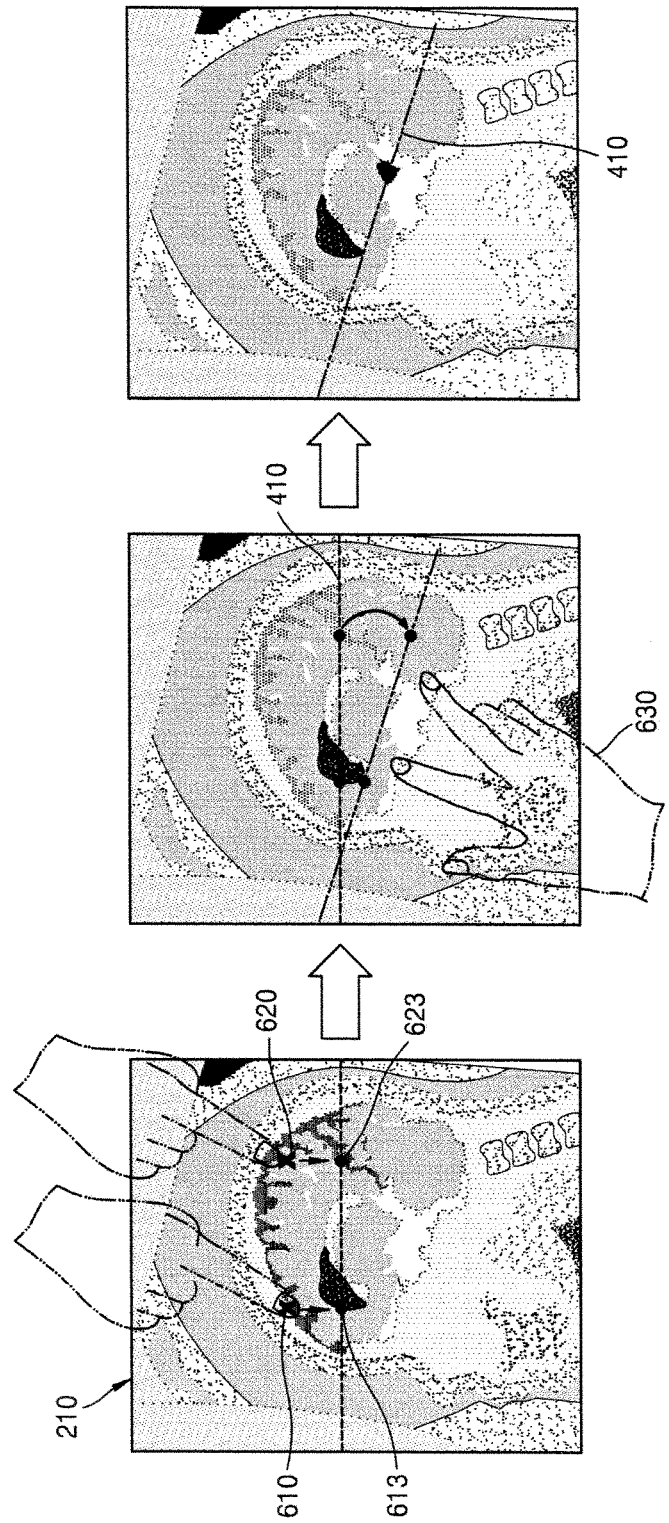

FIGS. 6A and 6B illustrate an example of a method of changing a plane selection line based on an external input, according to an embodiment of the present invention.

The method according to an embodiment of the present invention may further include an operation of selecting a first point from an acquired medical image according to a first external input and selecting a second point according to a second external input, an operation of generating a first plane selection line including the selected first and second points, and an operation of displaying information about a pattern which is set for changing at least one from among a direction and position of a plane selection line by the above-described method. The first plane selection line may be moved according to a third external input in the acquired medical image, based on the displayed information, and a plane image may be acquired along the moved first plane selection line.

For example, as illustrated in FIG. 6A, a first point 611 may be selected from a medical image 210 according to a first external input 610, and a second point 621 may be selected according to a second external input 620. The first and second external inputs 610 and 620 may include a click input using a cursor or a touch input on a touch screen. A first plane selection line 410 including the selected first and second points 611 and 621 may be generated. Also, information about a pattern which is set for changing at least one from among a direction and position of the generated first plane selection line 410 by the above-described method may be displayed. A user may change at least one from among the direction and position of the first plane selection line 410 by using a third input 630 with reference to the displayed information about the pattern for changing a line. The third input 630 may include a drag for the first plane selection line 410.

Moreover, as illustrated in FIG. 6B, a first point 613 may be selected from a medical image 210 according to a first external input 610, and a second point 623 may be selected according to a second external input 620. The first and second external inputs 610 and 620 may include a click input using a cursor or an input corresponding to a touch of a touch screen. The first point 613 which is selected according to the first external input 610 may be a point which is the closest to a point to which the first external input 610 is applied. For example, when the first external input 610 is applied by a user in the medical image 210, a point corresponding to a predetermined position may be selected. The point corresponding to the predetermined position may include a point in a first plane selection line 410 which is to be generated based on a pattern which is set by the above-described method.

The first plane selection line 410 including the selected first and second points 611 and 621 may be generated. Also, information about a pattern which is set for changing at least one from among a direction and position of the generated first plane selection line 410 by the above-described method may be displayed. The user may change at least one from among the direction and position of the first plane selection line 410 by using a third input 630 with reference to the displayed information about the pattern for changing a line. The third input 630 may include a drag for the first plane selection line 410.

Figure 7:
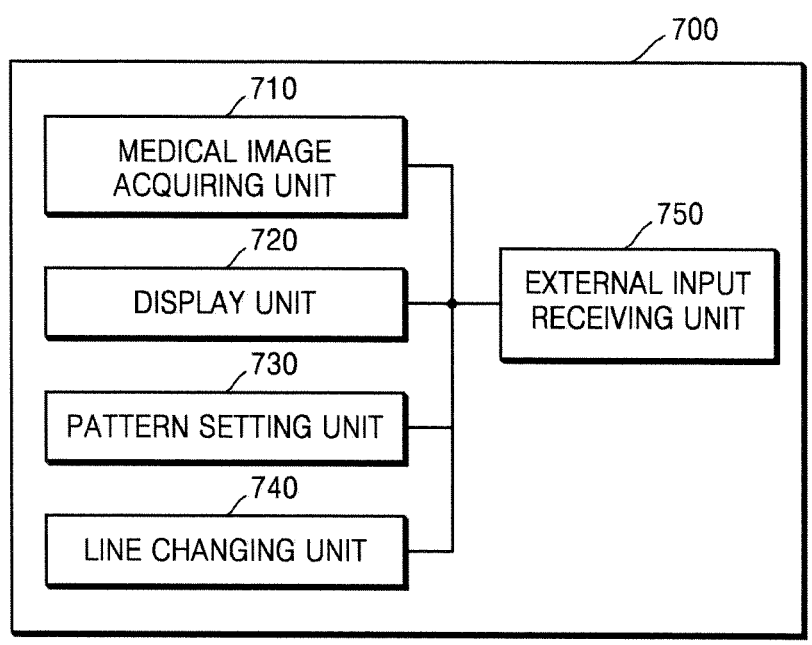
FIG. 7 is a block diagram illustrating an apparatus for changing at least one of a direction and position of a plane selection line, according to an embodiment of the present invention.

FIG. 7 is a block diagram illustrating an apparatus 700 for changing at least one from among a direction and position of a plane selection line, according to an embodiment of the present invention.

The apparatus 700 for changing at least one from among a direction and position of a plane selection line, according to an embodiment of the present invention, includes a medical image acquiring unit 710 that acquires a medical image of an object, a display 720 that displays a first plane image acquired along a first plane selection line of the medical image, a pattern setting device 730 that setting a pattern which is used to change at least one from among the direction and position of the plane selection line, and a line changing device 740 that changes at least one from among the direction and position of the plane selection line, based on the set pattern. The display displays a second plane image acquired along the changed plane selection line. The plane selection line according to an embodiment of the present invention may be automatically or manually selected based on an anatomical position of a part of interest, a measurement target item, and an anatomical view in the object.

The medical image may include a 2D image, a 3D volume image, or a dynamic image. The display 720 may display the medical image and first plane image of the object.

The pattern setting device 730 may determine an ROI including a first-direction plane selection line in the acquired medical image, generate at least one plane selection lines which have different directions or positions and are included in the determined ROI, extract the generated at least one plane selection lines, and generate the pattern in order where the at least one plane selection lines are extracted. The generated at least one plane selection lines may be removed according to an external input from a user.

The ROI 211 according to an embodiment of the present invention, as illustrated in FIG. 2A, may have a width-direction fan shape. For example, the ROI 211 may be determined as a region which is unfolded at a certain angle within a certain range with respect to the first-direction plane selection line 212. The certain angle and the certain range may be previously determined based on at least one from among the kind of examination and an examination item for the object. Also, the certain angle and the certain range may be set and adjusted according to an external input from the user.

The pattern setting device 730 may re-determine an ROI, regenerate at least one plane selection lines which have different directions or positions and are included in the re-determined ROI, re-extract the regenerated at least one plane selection lines, and regenerate the pattern in order where the at least one plane selection lines are re-extracted. An interval between the at least one plane selection lines when a plane selection line is regenerated may be denser than an interval of when the plane selection line is generated.

The pattern setting device 730 may extract the first plane selection line, for a first standard image to be acquired as the first plane image, extract a reference region from the acquired medical image, rotate the extracted first plane selection line by a certain angle based on the reference region to change the extracted first plane selection line to a second plane selection line, and generate, as the pattern, a rotation movement from the first plane selection line to the second plane selection line.

The pattern setting device 730 may generate at least one plane selection lines adjacent to the first plane selection line, extract the generated at least one plane selection lines, and generate the pattern in order where the at least one plane selection lines are extracted.

The pattern setting device 730 may extract the first plane selection line, for a first standard image to be acquired as the first plane image, generate at least one plane selection lines which are moved and disposed in a certain direction from the extracted first plane selection line, extract the generated at least one plane selection lines, and generate the pattern in order where the at least one plane selection lines are extracted. The certain direction may include at least one from among an up direction, a down direction, a left direction, a right direction, and a diagonal direction.

The pattern setting device 730 may extract a reference region from the acquired medical image, generate at least one plane selection lines which pass through the reference region and are within a certain angle range, extract the generated at least one plane selection lines, and generate the pattern in order where the at least one plane selection lines are rotated with respect to the reference region and extracted.

The apparatus 700 according to an embodiment of the present invention may further include an external input receiving unit 750. The pattern setting device 730 may generate at least one plane selection lines in order where an external input signal is applied, extract the at least one plane selection lines in order where the at least one plane selection lines are generated, and generate the pattern in order where the at least one plane selection lines are extracted.

The pattern setting device 730 may generate a second plane selection line adjacent to the first plane selection line, based on an external input signal, generate at least one plane selection lines which are provided between the first and second plane selection lines, sequentially extract at least one plane selection lines which are provided between the first and second selection lines, while moving lines in a certain direction from the first plane selection line to the second plane selection line, and generate a pattern for changing a line in order where the at least one plane selection lines are extracted. The certain direction may include at least one from among an up direction, a down direction, a left direction, a right direction, and a diagonal direction.

The pattern setting device 730 may load a pattern which is predetermined and is previously stored in a storage device, and set a pattern for changing at least one from among the direction and position of the plane selection line, based on the loaded pattern. The storage device may be included in the apparatus 700 according to an embodiment of the present invention, or may be provided in the outside and connected to the apparatus 700. For example, the storage device may be connected to the pattern setting device 730. For example, a pattern which is predetermined and is previously stored in a storage device may be loaded, and the loaded pattern may be set as a pattern for changing at least one from among a direction and position of a plane selection line. Also, the loaded pattern may be edited by the above-described method, and may be set as a pattern for changing at least one from among a direction and position of a plane selection line.

The line changing device 740 may change at least one from among the direction and position of the plane selection line based on the set pattern automatically or according to an external input.

The line changing device 740 may trace at least one from among the direction and position of the plane selection line which is changed based on the set pattern, and the display 720 may display a result of the tracing as a time-series image.

The pattern setting device 730 may select a first point from the acquired medical image according to a first external input, select a second point according to a second external input, generate a first plane selection line including the selected first and second points, and display information about a pattern which is set for changing at least one from among the direction and position of the plane selection line. The first plane selection line may be moved according to a third external input in the acquired medical image, based on the displayed information, and a plane image may be acquired along the moved first plane selection line.

The details of the above-described method may be equally applied to the apparatus according to an embodiment of the present invention. Thus, in the apparatus, the same details as those of the above-described method are not described.

The above-described embodiments of the present invention may be written as computer programs and may be implemented in general-use digital computers that execute the programs using a computer-readable recording medium. Examples of the computer-readable recording medium include magnetic storage media (e.g., ROM, floppy disks, hard disks, etc.) and optical recording media (e.g., CD-ROMs, or DVDs), etc).

It should be understood that the exemplary embodiments described herein should be considered in a descriptive sense only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims.

What is claimed is:

1. A method of changing at least one from among a direction and position of a plane selection line for acquiring an image of a plane of interest (POI) of an object, performed by an ultrasound diagnostic apparatus, the method comprising:
   acquiring a medical image of an object by receiving an echo signal based on an ultrasound wave, which is transmitted from a probe of the ultrasound diagnostic apparatus to the object;
   extracting a first plane selection line and a reference region from the acquired medical image;
   setting a pattern of at least one plane selection line to obtain the image of the plane of interest (POI) of the object, based on the first plane selection line and at least one second plane selection line, wherein the at least one second plane selection line is generated by rotating the first plane selection line by a certain angle based on the reference region or by moving the first plane selection line in a certain direction; and
   displaying at least one plane image obtained respectively along the at least one plane selection line, based on the set pattern,
   wherein the at least one plane selection line is selected based on an anatomical position of a part of interest, a measurement target item, and an anatomical view in the object.

2. The method of claim 1, wherein the medical image comprises a two-dimensional (2D) image, a three-dimensional (3D) volume image, or a dynamic image.

3. The method of claim 1, wherein the displaying at least one plane image comprises displaying both the medical image of the object and a first plane image acquired along the first plane selection line of the medical image.

4. The method of claim 1, wherein the extracting the first plane selection line and the reference region comprises:
  determining a region of interest (ROI) including a first-direction plane selection line in the acquired medical image, and
  wherein the setting the pattern of the least one plane selection line comprises:
  generating at least one plane selection lines which have different directions or positions and are included in the determined ROI;
  extracting the generated at least one plane selection lines; and
  generating the pattern in order where the at least one plane selection lines are extracted.

5. The method of claim 4, wherein the extracting the first plane selection line and the reference region comprises:
  re-determining an ROI,
  wherein the setting the pattern of the at least one plane selection line comprises:
  regenerating at least one plane selection lines which have different directions or positions and are included in the re-determined ROI;
  re-extracting the regenerated at least one plane selection line; and
  regenerating the pattern in order where the at least one plane selection line is re-extracted, and
  wherein an interval between the at least one plane selection line when a plane selection line is regenerated is denser than an interval of when the plane selection line is generated.

6. The method of claim 1, wherein the extracting the first plane selection line and the reference region comprises:
  extracting the first plane selection line, for a first standard image to be acquired as a first plane image; and
  extracting a reference region from the acquired medical image,
  wherein the setting the pattern of the at least one plane selection line comprises:
  rotating the extracted first plane selection line by a certain angle based on the reference region so as to change the extracted first plane selection line to the second plane selection line; and
  generating, as the pattern, a rotation movement from the first plane selection line to the second plane selection line.

7. The method of claim 1, wherein the setting the pattern of the at least one plane selection line comprises:
  generating at least one plane selection lines adjacent to the first plane selection line;
  extracting the generated at least one plane selection lines; and
  generating the pattern in order where the at least one plane selection lines are extracted.

8. The method of claim 1, wherein the extracting the first plane selection line and the reference region comprises:
  extracting the first plane selection line, for a first standard image to be acquired as the first plane image,
  wherein the setting the pattern of the at least one plane selection line comprises:
  generating at least one plane selection lines which are moved and disposed in a certain direction from the extracted first plane selection line;
  extracting the generated at least one plane selection lines; and
  generating the pattern in order where the at least one plane selection lines are extracted, and
  wherein the certain direction comprises at least one of an up direction, a down direction, a left direction, a right direction, and a diagonal direction.

9. The method of claim 1, wherein the extracting the first plane selection line and the reference region comprises:
  extracting a reference region from the acquired medical image, and
  wherein the setting the pattern of the at least one plane selection line comprises:
  generating at least one plane selection lines which pass through the reference region and are within a certain angle range;
  extracting the generated at least one plane selection lines; and
  generating the pattern in order where the at least one plane selection lines are rotated with respect to the reference region and extracted.

10. The method of claim 1, wherein the setting of the pattern of the at least one plane selection line comprises:
  generating at least one plane selection line in order where an external input signal is applied;
  extracting the at least one plane selection line in order where the at least one plane selection line is generated; and
  generating the pattern in order where the at least one plane selection line is extracted.

11. The method of claim 1, wherein the setting of the pattern of the at least one plane selection line comprises:
  generating the second plane selection line adjacent to the first plane selection line, based on an external input signal;
  generating at least one plane selection line which is provided between the first and second plane selection lines;
  sequentially extracting at least one plane selection lines, which is provided between the first and second selection lines, while moving lines in a certain direction from the first plane selection line to the second plane selection line; and
  generating a pattern for changing a line in order where the at least one plane selection lines are extracted,
  wherein the certain direction comprises at least one of an up direction, a down direction, a left direction, a right direction, and a diagonal direction.

12. The method of claim 1, wherein the setting of the pattern comprises loading a pattern which is predetermined and is previously stored in a storage device, and setting a pattern for changing at least one of the direction and position of the plane selection line, based on the loaded pattern.

13. The method of claim 1, further comprising:
  changing at least one of the direction and position of the at least one plane selection line based on the set pattern automatically or according to an external input.

14. The method of claim 1, further comprising:
  tracing at least one of the direction and position of the at least one plane selection line which is changed based on the set pattern; and
  displaying the trace result as a time-series image.

15. The method of claim 1, further comprising:
  selecting a first point from the acquired medical image according to a first external input and selecting a second point according to a second external input;
  generating a first plane selection line including the selected first and second points; and
  displaying information about a pattern which is set for changing at least one of the direction and position of the plane selection line, wherein,
the first plane selection line is moved according to a third external input in the acquired medical image, based on the displayed information, and
a plane image is acquired along the moved first plane selection line.

16. A non-transitory computer-readable storage medium storing a program for executing the method of claim 1.

17. An ultrasound diagnostic apparatus for changing at least one of a direction and position of a plane selection line for acquiring an image of a plane of interest (POI) of an object, the apparatus comprising:
a processor, coupled to a probe of the ultrasound diagnostic apparatus, configured to acquire a medical image of an object by receiving an echo signal based on an ultrasound wave, which is transmitted from the probe of the ultrasound diagnostic apparatus to the object;
extract a first plane selection line and a reference region from the acquired medical image; and
set a pattern of at least one plane selection line to obtain the image of the plane of interest (POI) of the object, based on the first plane selection line and at least one second plane selection line, wherein the at least one second plane selection line is generated by rotating the first plane selection line by a certain angle based on the reference region or by moving the first plane selection line in a certain direction; and
a display, coupled to the processor, configured to display at least one plane images obtained respectively along the at least one plane selection line, based on the set pattern,
wherein the at least one plane selection line is selected based on an anatomical position of a part of interest, a measurement target item, and an anatomical view in the object.

18. The ultrasound diagnostic apparatus of claim 17, wherein the medical image comprises a two-dimensional (2D) image, a three-dimensional (3D) volume image, or a dynamic image.

19. The ultrasound diagnostic apparatus of claim 17, wherein the display displays the medical image and a first plane image of the object.

20. The ultrasound diagnostic apparatus of claim 17, wherein the processor determines a region of interest (ROI) including a first-direction plane selection line in the acquired medical image, generates at least one plane selection lines which have different directions or positions and are included in the determined ROI, extracts the generated at least one plane selection lines, and generates the pattern in order where the at least one plane selection lines are extracted.

21. The ultrasound diagnostic apparatus of claim 20, wherein,
the processor re-determines an ROI, regenerates at least one plane selection lines which have different directions or positions and are included in the re-determined ROI, re-extracts the regenerated at least one plane selection lines, and regenerates the pattern in order where the at least one plane selection lines are re-extracted, and
an interval between the at least one plane selection lines when a plane selection line is regenerated is denser than an interval of when the plane selection line is generated.

22. The ultrasound diagnostic apparatus of claim 17, wherein the processor extracts the first plane selection line, for a first standard image to be acquired as a first plane image, extracts a reference region from the acquired medical image, rotates the extracted first plane selection line by a certain angle based on the reference region to change the extracted first plane selection line to the second plane selection line, and generates, as the pattern, a rotation movement from the first plane selection line to the second plane selection line.

23. The ultrasound diagnostic apparatus of claim 17, wherein the processor generates at least one plane selection lines adjacent to the first plane selection line, extracts the generated at least one plane selection lines, and generates the pattern in order where the at least one plane selection lines are extracted.

24. The ultrasound diagnostic apparatus of claim 17, wherein,
the processor extracts the first plane selection line, for a first standard image to be acquired as the first plane image, generates at least one plane selection line which is moved and disposed in a certain direction from the extracted first plane selection line, extracts the generated at least one plane selection lines, and generates the pattern in order where the at least one plane selection line is extracted, and
the certain direction comprises at least one of an up direction, a down direction, a left direction, a right direction, and a diagonal direction.

25. The ultrasound diagnostic apparatus of claim 17, wherein the processor extracts a reference region from the acquired medical image, generates at least one plane selection lines which pass through the reference region and are within a certain angle range, extracts the generated at least one plane selection line, and generates the pattern in order where the at least one plane selection line are rotated with respect to the reference region and extracted.

26. The ultrasound diagnostic apparatus of claim 17, further comprising an external input receiver,
wherein the processor generates at least one plane selection lines in order where an external input signal is applied, extracts the at least one plane selection lines in order where the at least one plane selection lines are generated, and generates the pattern in order where the at least one plane selection lines are extracted.

27. The ultrasound diagnostic apparatus of claim 17, further comprising an external input receiver,
wherein,
the processor generates the second plane selection line adjacent to the first plane selection line, based on an external input signal, generates at least one plane selection line which is provided between the first and second plane selection lines, sequentially extracts at least one plane selection line, which is provided between the first and second selection lines, while moving lines in a certain direction from the first plane selection line to the second plane selection line, and generates a pattern for changing a line in order where the at least one plane selection line is extracted, and
the certain direction comprises at least one of an up direction, a down direction, a left direction, a right direction, and a diagonal direction.

28. The ultrasound diagnostic apparatus of claim 17, wherein the processor loads a pattern which is predetermined and is previously stored in a storage device, and sets a pattern for changing at least one of the direction and position of the plane selection line, based on the loaded pattern.

29. The ultrasound diagnostic apparatus of claim 17, further comprising an external input receiving unit, wherein the processor changes at least one of the direction and position of the plane selection line based on the set pattern automatically or according to an external input.

30. The ultrasound diagnostic apparatus of claim 17, wherein, the processor traces at least one of the direction and position of the plane selection line which is changed based on the set pattern, and the display displays a result of the tracing as a time-series image.

31. The ultrasound diagnostic apparatus of claim 17, further comprising an external input receiving unit, wherein, the processor selects a first point from the acquired medical image according to a first external input, selects a second point according to a second external input, and generates a first plane selection line including the selected first and second points, the display displays information about a pattern which is set for changing at least one of the direction and position of the plane selection line, the first plane selection line is moved according to a third external input in the acquired medical image, based on the displayed information, and a plane image is acquired along the moved first plane selection line.

32. A method of changing at least one from among a direction and position of a plane selection line for acquiring an image of an object, performed by an ultrasound diagnostic apparatus, the method comprising:

receiving a first point and a second point from a medical image acquired from the ultrasound diagnostic apparatus;

generating a first plane selection line and a reference region to obtain the image of the plane of interest of the object, based on the first point and the second point;

generating a second plane selection line by rotating the first plane selection line by a certain angle based on the reference region, or by moving the first plane selection line in a certain direction; and displaying a second plane image acquired along the generated second plane selection line, wherein the first point and the second point indicates an anatomical position of a part of interest of the object, wherein the first plane selection line, the second plane selection line and information regarding a relationship between the first plane selection line and the second plane selection line are stored.

33. The method of claim 32, wherein the object is a fetus and the anatomical position of the part of interest of the object comprises a cavum septum pellucidum (CSP).

34. The method of claim 32, wherein the generating the second plane selection line comprises generating the second plane selection line based on a user input and the first plane selection line.

35. An ultrasound diagnostic apparatus, comprising:

a processor;

a display coupled to the processor; and a non-transitory computer-readable memory coupled to the processor and comprising programs that, when executed by the processor, perform operations comprising:

receiving a first point and a second point from a medical image acquired from the ultrasound diagnostic apparatus;

generating a first plane selection line and a reference region to obtain the image of the plane of interest of the object, based on the first point and the second point;

generating a second plane selection line by rotating the first plane selection line by a certain angle based on the reference region, or by moving the first plane selection line in a certain direction; and displaying a second plane image acquired along the generated second plane selection line, wherein the first point and the second point indicates an anatomical position of a part of interest of the object, wherein the first plane selection line, the second plane selection line and information regarding a relationship between the first plane selection line and the second plane selection line are stored.

* * * * *